(12) United States Patent
Jin et al.

(10) Patent No.: US 10,090,114 B2
(45) Date of Patent: Oct. 2, 2018

(54) TRIPHENYLAMINE DERIVATIVES AND PHOTOVOLTAIC DEVICE INCLUDING THE SAME

(71) Applicants: PUSAN NATIONAL UNIVERSITY INDUSTRY-UNIVERSITY COOPERATION FOUNDATION, Busan (KR); KOREA INSTITUTE OF MACHINERY AND MATERIALS, Daejeon (KR)

(72) Inventors: Sung Ho Jin, Busan (KR); Myung Kwan Song, Ulsan (KR)

(73) Assignees: PUSAN NATIONAL UNIVERSITY INDUSTRY—UNIVERSITY COOPERATION FOUNDATION, Busan (KR); KOREA INSTITUTE OF MACHINERY AND MATERIALS, Daejeon (KR)

( * ) Notice: Subject to any disclaimer, the term of this patent is extended or adjusted under 35 U.S.C. 154(b) by 65 days.

(21) Appl. No.: 15/359,935

(22) Filed: Nov. 23, 2016

(65) Prior Publication Data

US 2017/0194103 A1    Jul. 6, 2017

(30) Foreign Application Priority Data

Nov. 16, 2015    (KR) .................. 10-2015-0160230

(51) Int. Cl.
*H01B 1/12*    (2006.01)
*H01G 9/20*    (2006.01)
(Continued)

(52) U.S. Cl.
CPC ......... *H01G 9/2018* (2013.01); *C07C 215/68* (2013.01); *C07D 471/16* (2013.01);
(Continued)

(58) Field of Classification Search
CPC ... C07C 215/68; C07D 471/16; C07F 7/0812; C07F 7/0818; H01G 9/2018;
(Continued)

(56) References Cited

U.S. PATENT DOCUMENTS

2009/0295275 A1* 12/2009 Parham ................ C07D 471/16
                                                                313/504

FOREIGN PATENT DOCUMENTS

CN        104530391 A       4/2015
KR    1020100048447 A       5/2010
(Continued)

OTHER PUBLICATIONS

Jiang et al., "A Fully Diarylmethylene-Bridged Triphenylamine Derivative as Novel Host for Highly Efficient Green Phosphorescent OLEDs" Org. Lett. 11(7), pp. 1503-1506 (2009) (Year: 2009).*
(Continued)

*Primary Examiner* — Mark Kopec
*Assistant Examiner* — Jaison P Thomas
(74) *Attorney, Agent, or Firm* — STIP Law Group, LLC

(57) ABSTRACT

Provided are a hole transporting material for a photovoltaic device and a photovoltaic device including the same, wherein the hole transporting material is a triphenylamine derivative into which a specific substituent is introduced. The triphenylamine derivative into which the specific substituent is introduced according to the present invention is used as a material of a hole transport layer of the photovoltaic device to exhibit improved power conversion efficiency than those of the existing materials. The triphenylamine derivative into which the specific substituent is introduced according to the present invention has high hole mobility, an appropriate energy level, thermal stability, and good solubility due to a structural characteristic, and when the triphenylamine derivative is applied as the hole transporting
(Continued)

material of the photovoltaic device, particularly, a perovskite solar cell, or an organic solar cell, excellent power conversion efficiency and device stability are exhibited as compared to the existing hole transporting material, Spiro-OMeTAD or PEDOT:PSS mixture.

7 Claims, 17 Drawing Sheets

(51) Int. Cl.
| | |
|---|---|
| C07C 215/68 | (2006.01) |
| C07D 471/16 | (2006.01) |
| C07F 7/08 | (2006.01) |
| H01L 51/00 | (2006.01) |
| H01L 51/42 | (2006.01) |
| H01L 31/0256 | (2006.01) |

(52) U.S. Cl.
CPC .......... *C07F 7/0812* (2013.01); *C07F 7/0818* (2013.01); *H01B 1/12* (2013.01); *H01L 51/0059* (2013.01); *H01L 51/0072* (2013.01); *H01L 51/0077* (2013.01); *H01L 51/0094* (2013.01); *H01L 51/4233* (2013.01); *H01L 51/4213* (2013.01); *H01L 2031/0344* (2013.01); *H05K 999/99* (2013.01); *Y02E 10/549* (2013.01)

(58) Field of Classification Search
CPC ......... H01L 2031/0344; H01L 51/0059; H01L 51/0072; H01L 51/0077; H01L 51/0094; H01L 51/4213; H01B 1/12
See application file for complete search history.

(56) References Cited

FOREIGN PATENT DOCUMENTS

| | | |
|---|---|---|
| KR | 1020110087613 | 8/2011 |
| KR | 1020130045298 | 5/2013 |
| KR | 1408246 | 6/2014 |

OTHER PUBLICATIONS

Songtao LV et al., Simple Triphenylamine-Based Hole-Transporting Materials for Perovskite Solar Cells, Electrochimica Acta, Oct. 9, 2015, pp. 733-741, vol. 182, Elsevier, Netherlands.
Office Action from the Korea Patent Office, dated Feb. 20, 2017.

* cited by examiner

TRIPHENYLAMINE DERIVATIVES AND PHOTOVOLTAIC DEVICE INCLUDING THE SAME

CROSS-REFERENCE TO RELATED APPLICATIONS

This application claims priority under 35 U.S.C. § 119 to Korean Patent Application No. 10-2015-0160230, filed on Nov. 16, 2015, in the Korean Intellectual Property Office, the disclosure of which is incorporated herein by reference in its entirety.

TECHNICAL FIELD

The following disclosure relates to a hole transporting material for a photovoltaic device and a photovoltaic device including the same.

BACKGROUND

A solar cell technology is to directly convert light, that is, solar energy into electric energy by utilizing a photovoltaic effect, and most commercialized solar cells are inorganic solar cells using inorganic materials such as silicon. However, the inorganic solar cells have disadvantages in that manufacturing cost is increased due to a complicated manufacturing process, and high-priced materials are required, and accordingly, research into a dye-sensitized solar cell and an organic solar cell manufactured with low cost through a relatively simple manufacturing process and with low-priced materials has been actively conducted.

In general, the dye-sensitized solar cell consists of two electrodes (a photo electrode and a counter electrode), semiconductor nanoparticles (mainly titanium dioxide), dye, and a liquid electrolyte. When solar light (visible light) is absorbed onto an n-type nanoparticle semiconductor oxide electrode having a surface onto which dye molecules are chemically adsorbed, the dye molecules form electron-hole pairs, wherein the electrons are injected into a conduction band of semiconductor oxide and are transferred to a transparent conductive film through interfaces between nanoparticles, thereby generating a current, and the holes receive the electrons by an oxidation-reduction electrolyte and are reduced again. The dye-sensitized solar cell is operated by the electron circulation mechanism as described above. The dye-sensitized solar cell using high-priced ruthenium-based complex as a dye according to the related art has received academic attention due to an energy conversion efficiency of over 10%, but has difficulty in commercialization due to a problem that long-term stability of a device is deteriorated.

Regarding this, a liquid electrolyte component part is very closely related to the long-term stability of the device. A volatile electrolyte solution in a solution state containing iodine has an excellent advantage in view of an energy conversion efficiency, but also has a disadvantage that if the electrolyte leaks or becomes volatile during use time, a fatal problem in stability of the device may occur. In particular, an iodine component of the electrolyte solution may cause chemical decomposition of the dye molecules, and may seriously destroy a module grid of the metal component due to an action between a small amount of oxygen and moisture when the cell is operated for a long time.

As a method for solving the problem of the dye-sensitized solar cell by the liquid electrolyte, The Gratzel Group in Switzerland reported in 2013 that 7.2% energy conversion efficiency could be obtained by using Y123 organic dye, and substituting the existing liquid electrolyte with a solid type hole conductive organic material, 2,2',7,7'-tetrakis(N,N-di-p-methoxyphenyl-amine)9,9'-spirobifluorene (Spiro-OMeTAD), which had the highest value of efficiency of the solid type dye-sensitized solar cell reported to date, but it was lower than an energy conversion efficiency of the existing dye-sensitized solar cell using the liquid electrolyte solution.

Meanwhile, the organic solar cell is composed of a first electrode, a photoactive layer consisting of an electron donor (D) and an electron acceptor (A), and a second electrode, and may further include an electron transport layer and a hole transport layer. When light is projected to the organic solar cell, positive charges (holes) and negative charges (electrons) are produced in the photoactive layer, the electrons are moved to an electrode of an upper part of the photoactive layer, and the holes are moved to the hole transport layer. The hole transport layer of the organic solar cell manufactured by using a mixture of poly(3,4-ethylene-dioxy-thiophene) (PEDOT) and poly(styrenesulfonate) (PSS) according to the related art causes corrosion of a lower electrode layer consisting of a metal such as ITO due to high acidity of PEDOT:PSS, and as a result, lifespan of the hole transport layer is reduced, which is recognized as a problem in commercialization of the organic solar cell.

Accordingly, it needs to design and develop a novel hole transporting material of an organic material-based small molecule capable of substituting the existing hole transporting material, PEDOT:PSS, in order to improve the power conversion efficiency and the lifespan of the device in the organic solar cell.

Meanwhile, the perovskite solar cell has received attention as an important device due to excellent photovoltaic properties, cost reduction, and easy processes. The perovskite solar cell without the hole transporting material had a low charge extraction and charge recombination at an interface as compared to the perovskite solar cell including the hole transporting material, resulting in a drop of an open-circuit voltage and a charging rate. Therefore, in order to have higher power conversion efficiency (PCE), it is required to increase the charge extraction and to mitigate unwanted charge recombination at the interface. To this end, a role of the hole transporting material (HTM) is important in the perovskite solar cell.

A research into a technology of better improving the power conversion efficiency which is one of the main characteristics of the perovskite solar cell has been conducted. Recently, a power conversion efficiency of the perovskite solar cell using spiro-OMeTAD as the hole transporting material was achieved to be 20%. However, the spiro-OMeTAD has a complicated synthesis, a high price, and a low carrier mobility of charges, which may be limited in commercialization of the perovskite solar cell. A hole transporting material based on a polymer has been also widely used, but has problems in that stability of a device may be deteriorated due to acid environment, and there is difficulty in reproducibly and uniformly controlling factors such as a molecular weight of the polymer, polydispersity, and stereoregularity that directly affect performances of the solar cell, synthesis or purification process is complicated, and charge mobility is low.

In general, dopants such as Li-TFSI, t-BP, etc., are added to improve the power conversion efficiency in the perovskite solar cell. However, it is required to design and develop a novel hole transporting material of the organic material-based small molecule which is effective without including the dopants in order to secure device stability of the perovskite solar cell.

RELATED ART DOCUMENT (Patent Document 1) Korean Patent Laid-Open Publication No. 10-2013-0045298
(Patent Document 2) Korean Patent Laid-Open Publication No. 10-2011-0087613
(Patent Document 3) Korean Patent No. 1408246

SUMMARY

The present inventors studied a technology of improving efficiency and stability by using a novel hole transporting material in a perovskite solar cell and an organic solar cell, synthesized a triphenylamine derivative into which a specific substituent is introduced, and found that efficiency and stability of the solar cells are enhanced when the triphenylamine derivative is used as the hole transporting material in the perovskite solar cell and the organic solar cell, and completed the present invention.

An embodiment of the present invention is directed to providing a novel triphenylamine derivative.

Another embodiment of the present invention is directed to providing a triphenylamine derivative as a hole transporting material having a novel structure which is usable for a photovoltaic device.

Another embodiment of the present invention is directed to providing a photovoltaic device including the novel triphenylamine derivative.

The present invention relates to a hole transporting material having a novel structure capable of enhancing efficiency and stability of a photovoltaic device, and a photovoltaic device including the same, and more specifically, a triphenylamine derivative into which a specific substituent is introduced as the hole transporting material of the present invention, and a photovoltaic device having an enhanced device efficiency and stability including the triphenylamine derivative.

In one general aspect, there is provided a triphenylamine derivative represented by Chemical Formula 1 below:

[Chemical Formula 1]

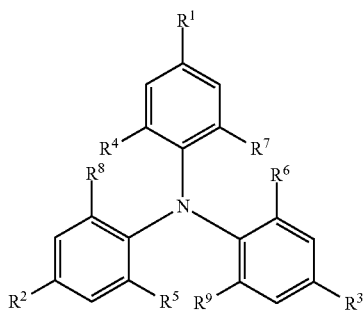

in Chemical Formula 1,
$R^1$, $R^2$ and $R^3$ are each independently hydrogen, (C1-20)alkyl, (C1-20)alkoxy, or (C1-20)alkylsilyl;
$R^4$, $R^5$, $R^6$, $R^7$, $R^8$ and $R^9$ are each independently hydrogen or —C($L^1R^{11}$)($L^2R^{12}$)(OH), or $R^4$ and $R^8$, $R^5$ and $R^9$, and $R^6$ and $R^7$ may be linked to each other to form —C($L^1R^{11}$) ($L^2R^{12}$)—;

$L^1$ and $L^2$ are each independently (C6-20)arylene;
$R^{11}$ and $R^{12}$ are each independently hydrogen, (C1-20)alkyl, (C1-20)alkoxy, or (C1-20)alkylsilyl; and
provided that $R^4$ and $R^7$ are not the same, $R^5$ and $R^8$ are not the same, and $R^6$ and $R^9$ are not the same.

In the triphenylamine derivative represented by Chemical Formula 1 according to an exemplary embodiment of the present invention, $R^1$, $R^2$ and $R^3$ may be each independently hydrogen or (C1-20)alkyl.

The triphenylamine derivative represented by Chemical Formula 1 according to an exemplary embodiment of the present invention may be represented by Chemical Formula 2 or 3 below:

[Chemical Formula 2]

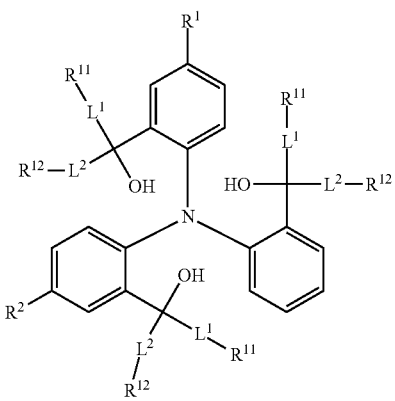

[Chemical Formula 3]

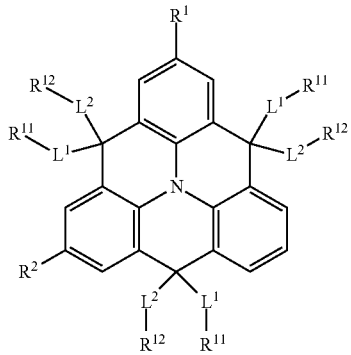

in Chemical Formulas 2 and 3, $R^1$, $R^2$, $L^1$, $L^2$, $R^{11}$ and $R^{12}$ are the same as defined in Chemical Formula 1 above.

In the triphenylamine derivative represented by Chemical Formulas 2 and 3 according to an exemplary embodiment of the present invention, $R^1$ and $R^2$ may be each independently (C1-20)alkyl; $L^1$ and $L^2$ may be each independently (C6-20)arylene; and $R^{11}$; and $R^{12}$ may be each independently (C1-20)alkoxy, or (C1-20)alkylsilyl.

In the triphenylamine derivative represented by Chemical Formulas 2 and 3 according to an exemplary embodiment of the present invention, $R^1$ and $R^2$ may be each independently methyl, ethyl, propyl, butyl, pentyl or hexyl; $L^1$ and $L^2$ may be each independently phenylene, biphenylene, terphenylene, naphthylene, phenanthrenylene, anthracenylene or perylenylene; and $R^{11}$ and $R^{12}$ may be each independently methoxy, ethoxy, propoxy, butoxy, pentoxy, hexyloxy, ethylhexyloxy, trimethylsilyl, triethylsilyl or methylethylsilyl.

The triphenylamine derivative according to an exemplary embodiment of the present invention may be selected from the following structures, but is not limited thereto:

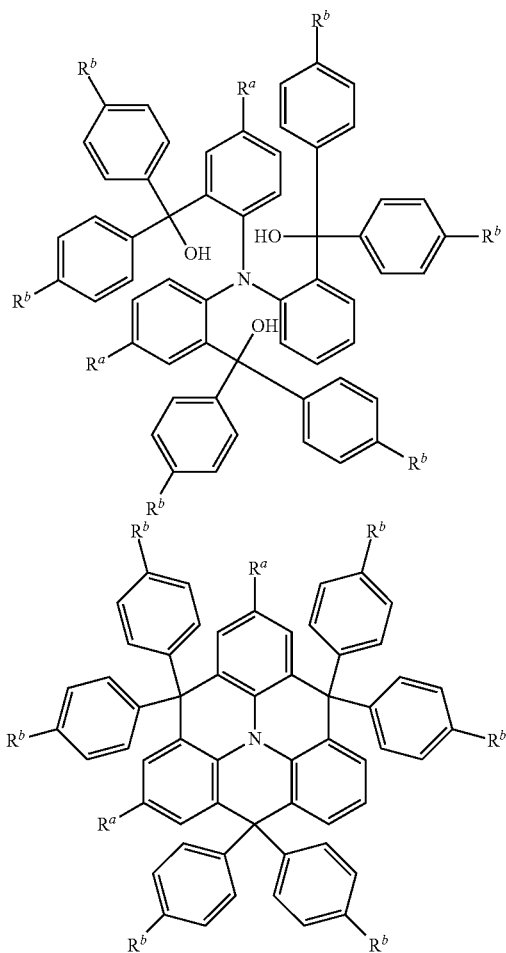

$R^a$ is butyl, and $R^b$ is ethylhexyloxy or trimethylsilyl.

In addition, in another general aspect, there is provided a photovoltaic device including the triphenylamine derivative represented by Chemical Formula 1.

The photovoltaic device according to an exemplary embodiment of the present invention may include the triphenylamine derivative represented by Chemical Formula 1 as a hole transporting material.

The photovoltaic device according to an exemplary embodiment of the present invention may be an organic/inorganic hybrid perovskite solar cell, an organic solar cell, an organic light-emitting diode, or a photodetector.

The photovoltaic device according to an exemplary embodiment of the present invention may be an organic/inorganic hybrid perovskite solar cell including the triphenylamine derivative represented by Chemical Formula 1 and at least one additive selected from t-BP (t-butyl pyridine) and Li-TFSI (lithium bis(trifluoro methanesulfonyl) imide.

DETAILED DESCRIPTION OF EMBODIMENTS

Figure 1:
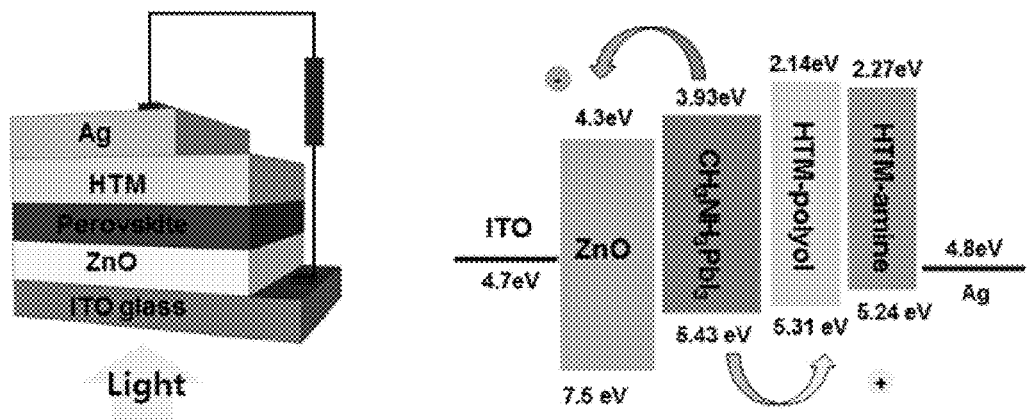
FIG. 1 is a chart illustrating a structure and an energy level of a perovskite solar cell.

Hereinafter, the present invention is described in detail. Meanwhile, unless technical and scientific terms used herein are defined otherwise, they have meanings understood by those skilled in the art to which the present invention pertains. Known functions and components will be omitted so as not to obscure the description of the present invention with unnecessary detail.

In one general aspect, there is provided a triphenylamine derivative represented by Chemical Formula 1 below:

[Chemical Formula 1]

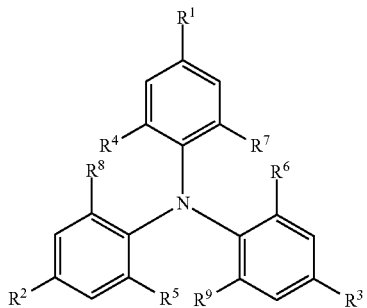

[Chemical Formula 2]

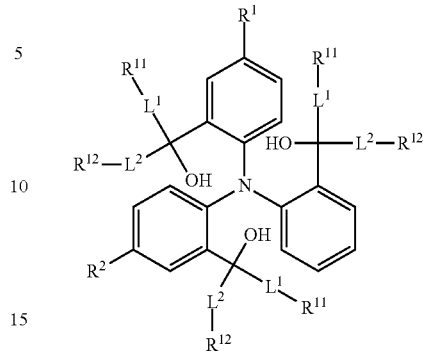

[Chemical Formula 3]

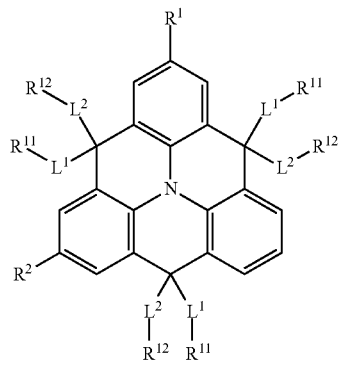

in Chemical Formula 1, $R^1$, $R^2$ and $R^3$ are each independently hydrogen, (C1-20) alkyl, (C1-20)alkoxy, or (C1-20)alkylsilyl;

$R^4$, $R^5$, $R^6$, $R^7$, $R^8$ and $R^9$ are each independently hydrogen or —C($L^1R^{11}$)($L^2R^{12}$)(OH), or $R^4$ and $R^8$, $R^5$ and $R^9$, and $R^6$ and $R^7$ may be linked to each other to form —C($L^1R^{11}$) ($L^2R^{12}$)—;

$L^1$ and $L^2$ are each independently (C6-20)arylene;

$R^{11}$ and $R^{12}$ are each independently hydrogen, (C1-20)alkyl, (C1-20)alkoxy, or (C1-20)alkylsilyl; and provided that $R^4$ and $R^7$ are not the same, $R^5$ and $R^8$ are not the same, and $R^6$ and $R^9$ are not the same.

The triphenylamine derivative represented by Chemical Formula 1 of the present invention has a structure in which one di(substituted or unsubstituted aryl)(hydroxy)methyl group is necessarily introduced at an ortho position of each phenyl group bonded to a nitrogen atom or a structure in which carbon atoms at the ortho position of each phenyl group are linked to each other via the di(substituted or unsubstituted aryl)methylene to form a fused ring. Due to the structural characteristic, excellent power conversion efficiency and device stability are exhibited as compared to the existing hole transporting material, that is, Spiro-OMeTAD or PEDOT:PSS mixture when the triphenylamine derivative is applied as the hole transporting material of the photovoltaic device, particularly, the perovskite solar cell or the organic solar cell.

In addition, the triphenylamine derivative of the present invention is a single molecule, and therefore, a compound having high purity may be obtained since synthesis and separation thereof are significantly easy due to the single molecule, unlike the existing polymer hole transport compounds, thereby having a significantly high advantage for commercial application.

The alkyl group or alkoxy group included in substituents described in the present invention may have a linear form or a branched form.

In the triphenylamine derivative represented by Chemical Formula 1 according to an exemplary embodiment of the present invention, preferably, $R^1$, $R^2$ and $R^3$ may be each independently hydrogen or (C1-20)alkyl.

More preferably, the triphenylamine derivative represented by Chemical Formula 1 may be represented by Chemical Formula 2 or 3 below:

in Chemical Formulas 2 and 3, $R^1$, $R^2$, $L^1$, $L^2$, $R^{11}$ and $R^{12}$ are the same as defined in Chemical Formula 1 above.

In the triphenylamine derivative represented by Chemical Formulas 2 and 3 according to an exemplary embodiment of the present invention, in view of excellent power conversion efficiency and lifespan characteristics, preferably, $R^1$ and $R^2$ may be each independently (C1-20)alkyl; $L^1$ and $L^2$ may be each independently (C6-20)arylene; and $R^{11}$ and $R^{12}$ may be each independently (C1-20)alkoxy, or (C1-20)alkylsilyl.

In the triphenylamine derivative represented by Chemical Formulas 2 and 3 according to an exemplary embodiment of the present invention, in view of improvement in solubility, $R^{11}$; and $R^{12}$ may be each independently (C1-20)alkoxy.

In the triphenylamine derivative represented by Chemical Formulas 2 and 3 according to an exemplary embodiment of the present invention, specifically, $R^1$ and $R^2$ may be each independently methyl, ethyl, propyl, butyl, pentyl or hexyl; $L^1$ and $L^2$ may be each independently phenylene, biphenylene, terphenylene, naphthylene, phenanthrenylene, anthracenylene or perylenylene; and $R^{11}$ and $R^{12}$ may be each independently methoxy, ethoxy, propoxy, butoxy, pentoxy, hexyloxy, ethylhexyloxy, trimethylsilyl, triethylsilyl or methylethylsilyl.

The triphenylamine derivative according to an exemplary embodiment of the present invention may be selected from the following structures, but is not limited thereto:

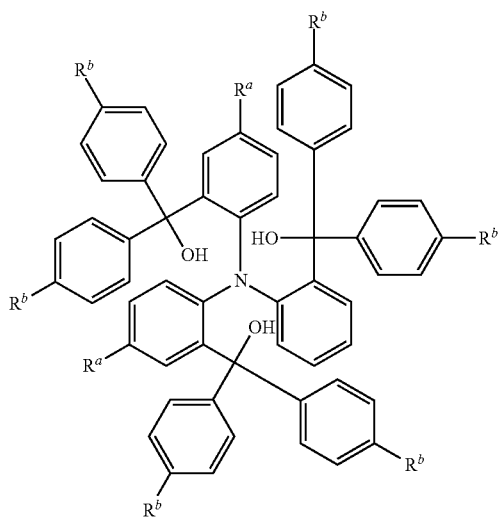

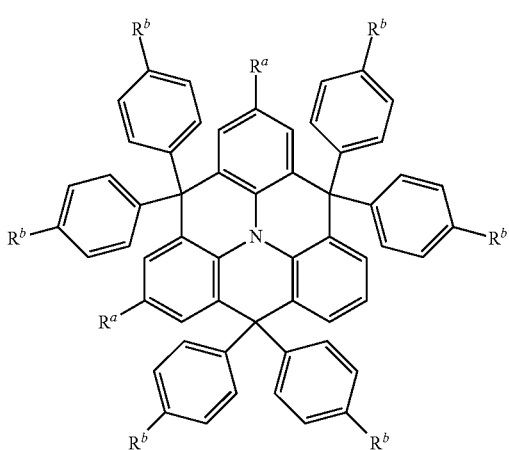

$R^a$ is butyl, and $R^b$ is ethylhexyloxy or trimethylsilyl.

The triphenylamine derivative of the present invention may be prepared, for example, by Reaction Scheme 1 below. The preparation thereof is described through Examples 1 to 2 in more detail. However, the preparation method of the triphenylamine derivative of the present invention is not limited to the Reaction Scheme 1 below, but the triphenylamine derivative may be synthesized by various methods using organic reactions known in the art:

[Reaction Scheme 1]

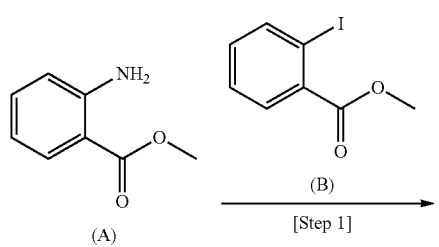

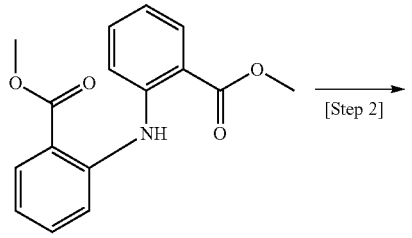

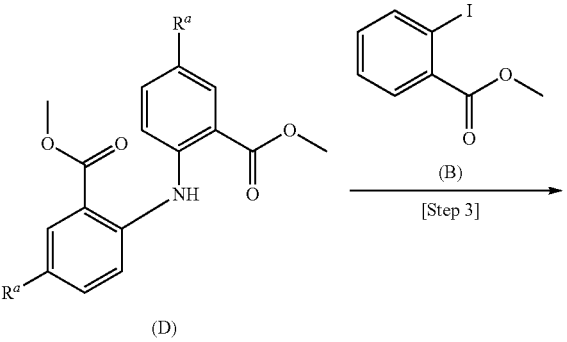

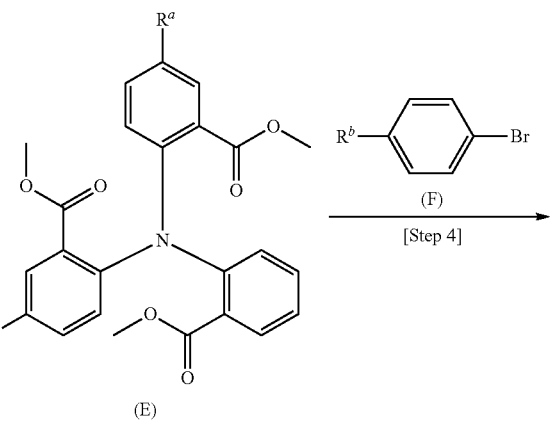

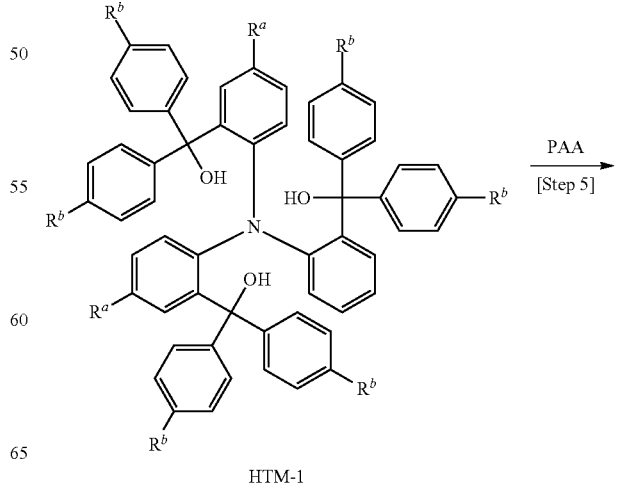

HTM-1

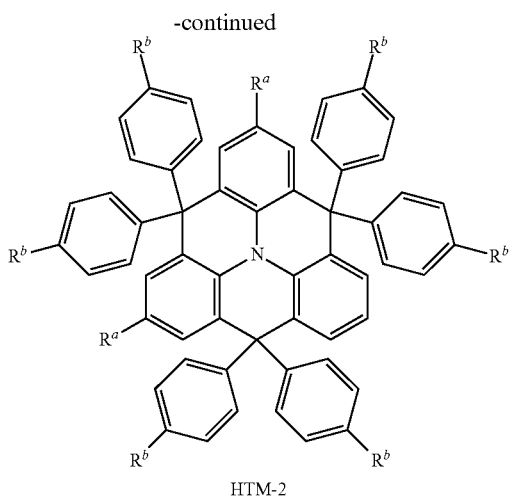

HTM-2 in Reaction Scheme 1, $R^a$ is (C1-20)alkyl, and $R^b$ is (C1-20)alkoxy or (C1-20)alkylsilyl.

The Reaction Scheme 1 includes preparing dimethyl 2,2'-azanediyldibenzoate (Compound C) by reacting methyl 2-aminobenzoate (Compound A) with methyl 2-iodobenzoate (Compound B) (Step 1); preparing dimethyl 6,6'-azanediylbis(3-alkylbenzoate) (Compound D) by Friedel-Craft alkylation reaction of the prepared dimethyl 2,2'-azanediyldibenzoate (Compound C) and alkylchloride represented by $R^a$—Cl (Step 2); preparing dimethyl 6,6'-(2-(methoxycarbonyl)phenylazanediyl)bis(3-alkylbenzoate) (Compound E) by reacting the prepared dimethyl 6,6'-azanediylbis(3-alkylbenzoate) (Compound D) with methyl 2-iodobenzoate (Compound B) (Step 3); preparing HTM-1 by reacting 1-bromo-4-(alkoxy or alkylsilyl)benzene (Compound F) with magnesium to prepare 4-(alkoxy or alkylsilyl) phenyl)magnesium bromide, followed by reacting with the dimethyl 6,6'-(2-(methoxycarbonyl)phenylazanediyl)bis(3-alkylbenzoate) (Compound E) prepared in Step 3 (Step 4); and preparing HTM-2 by cyclizing the prepared HTM-1 under PPA (polyphosphoric acid) (Step 5).

The triphenylamine derivative represented by Chemical Formula 1 according to the present invention has unique characteristics such as high hole mobility, an appropriate energy level, thermal stability, and good solubility, and may be effectively used as the hole transporting material of the photovoltaic device. Therefore, the present invention provides a photovoltaic device including the triphenylamine derivative represented by Chemical Formula 1.

The photovoltaic device according to an exemplary embodiment of the present invention may include the triphenylamine derivative represented by Chemical Formula 1 as the hole transporting material.

The photovoltaic device according to an exemplary embodiment of the present invention may be an organic/inorganic hybrid perovskite solar cell, an organic solar cell, an organic light-emitting diode, or a photodetector.

In an exemplary embodiment of the present invention, the organic/inorganic hybrid perovskite solar cell may have the following configurations, but the configuration is not limited thereto:

a first electrode including a conductive transparent substrate;

an electron transport layer formed on the first electrode;

a light absorption layer formed on the electron transport layer;

a hole transport layer formed on the photoactive layer; and a second electrode formed on the hole transport layer.

The first electrode including the conductive transparent substrate may be a glass substrate or a plastic substrate including a transparent electrode formed of at least one material selected from the group consisting of indium tin oxide (ITO), fluorine tin oxide (FTO), ZnO—Ga$_2$O$_3$, ZnO—Al$_2$O$_3$ and tin-based oxides.

The electron transport layer is a metal oxide layer including metal oxide, wherein the metal oxide may be nanoparticle oxides such as titanium dioxide (TiO$_2$), tin dioxide (SnO$_2$), zinc oxide (ZnO), etc., but is not limited thereto.

The light absorption layer is a perovskite layer including a compound having a perovskite crystalline structure, wherein the compounds having a perovskite structure may be one or two or more selected from H$_3$NH$_3$PbI$_x$Cl$_y$, (x is a real number satisfying 0≤x≤3, y is a real number satisfying 0≤y≤3, and x+y=3), CH$_3$NH$_3$PbI$_x$Br$_y$, (x is a real number satisfying 0≤x≤3, y is a real number satisfying 0≤y≤3, and x+y=3), CH$_3$NH$_3$PbClBr$_y$, (x is a real number satisfying 0≤x≤3, y is a real number satisfying 0≤y≤3, and x+y=3), and CH$_3$NH$_3$PbI$_x$F$_y$, (x is a real number satisfying 0≤x≤3, y is a real number satisfying 0≤y≤3, and x+y=3).

The hole transport layer may include the triphenylamine derivative of the present invention as the hole transporting material, and may further include at least one additive selected from t-BP (t-butyl pyridine) and Li-TFSI (lithium bis(trifluoro methanesulfonyl)imide) as a dopant.

As the second electrode, Au, Ag, Al, etc., may be used. The second electrode may be deposited on the hole transport layer mainly through a heat deposition method.

Meanwhile, an open-circuit voltage of the solar cell mostly depends on a difference between highest occupied molecular orbital (HOMO) of electron donors and lowest unoccupied molecular orbital (LUMO) of electron acceptors. The HOMO energy level of the triphenylamine derivative of the present invention thoroughly fits with an energy level of CH$_3$NH$_3$PbI$_3$ (−5.43 eV) that may be included in the perovskite layer of the solar cell, such that favorable charge separation and charge transfer at the interface of the perovskite layer and the transport layer may be expected. Accordingly, as compared to the spiro-OMeTAD (HOMO, −5.22 eV) which is the hole transporting material generally used in the art, the HOMO energy level of the present invention is more easily and effectively moved from the perovskite layer to the triphenylamine derivative of the present invention which is the material of the hole transport layer. That is, when considering that the open-circuit voltage depends on the difference between the HOMO level of the hole transporting material and a quasi-Fermi level of the metal oxide layer, from harmony of the HOMO level as described above, the triphenylamine derivative of the present invention has much higher power conversion efficiency as compared to the existing spiro-OMeTAD.

In general, the organic solar cell has a metal/organic semiconductor (photoactive layer)/metal (that is, metal-semiconductor or insulator-metal: MSM) structure and has a high work function, and includes transparent electrode, indium tin oxide as a cathode, and Al, Ca, or the like, having a low work function as an anode. The hole transport layer may be inserted between the cathode and the photoactive layer and the electron transport layer may be inserted between the anode and the photoactive layer.

The photoactive layer has a bulk-heterojunction structure obtained by mixing electron donors (D) with electron acceptors (A). A manufacturing method of the photoactive layer is simple, and a surface area at D/A (donor/acceptor) interface is largely increased, such that possibility of the charge separation is increased, and an efficiency in charge collection as electrodes is also increased.

The organic solar cell according to the present invention preferably has a BHJ structure. Examples of the electron donors may include P3HT (poly 3-hexylthiophene), PTB7 (Poly[4,8-bis[(2-ethylhexyl) oxy]benzo[1,2-b:4,5-b']dithiophene-2,6-diyl][3-fluoro-2-[(2-ethylhexyl)carbonyl]thieno[3,4-b]thiophenediyl]), PCPDTBT (poly(2,6-(4,4-bis-(2-ethylhexyl)-4H-cyclopenta[2,1-b;3,4-b]dithiophene)-alt-4,7 (2,1,3-benzothiadiazole)), PCPTBT (poly (N-9"-heptadecanyl-2,7-carbazole-alt-5,5-(4',7'-di-2-thienyl-2',1',3'-benzothiadiazole)), MDMO-PPV (poly[2-methoxy-5-(3',7'-dimethyloctyloxy)]-1,4-phenylene vinylene), MEH-PPV (poly[2-methoxy-5-(2"-ethylhexyloxy)-p-phenylene vinylene]), etc. Examples of the electron acceptors may include C60, C70, PCBM (Phenyl C61-butyric acid methyl ester), [70]PCBM (Phenyl $C_{71}$-butyric acid methyl ester), [60]ICBA (Indene-C60 Bis-Adduct), PCBCR (phenyl-C61-butyric acid cholestryl ester), [70]PCBCR (phenyl-$C_{71}$-butyric acid cholestryl ester), perylene, PBI (polybenzimidazole), PTCBI (3,4,9,10-perylene-tetracarboxylic bis-benzimidazole), etc. However, the electron donors and the electron acceptors are not limited to the above-described examples.

In a general organic solar cell, the electrons are released to the anode, and the holes are released to the cathode, and on the contrary, in an inverted organic solar cell, the electrons are released to the cathode, and the holes are released to the anode. The general organic solar cell usually uses PEDOT:PSS as the hole transport layer, such that an acid layer is formed due to high acidity, and accordingly, the general organic solar cell has disadvantages in that lifespan of the device is short. In addition, since an oxidation speed of electrodes of Al, etc., is rapid, the lifespan of the device is more decreased, such that the inverted organic solar cell which is a more stable device is more preferred.

In an exemplary embodiment of the present invention, the organic solar cell is the inverted organic solar cell, and may have the following configuration:

a first electrode including a glass substrate;
a metal oxide layer formed on the first electrode;
a photoactive layer formed on the metal oxide layer;
a hole transport layer formed on the photoactive layer; and
a second electrode formed on the hole transport layer.

Hereinafter, the present invention will be described in more detail with reference to the Examples below. The following Examples are provided for illustration, and therefore, the scope of the present invention is not limited to only the following Examples.

Examples 1 to 2: Preparation of Hole Transporting Material

[Example 1] Preparation of HTM-Polyol and HTM-Amine that are Hole Transporting Materials

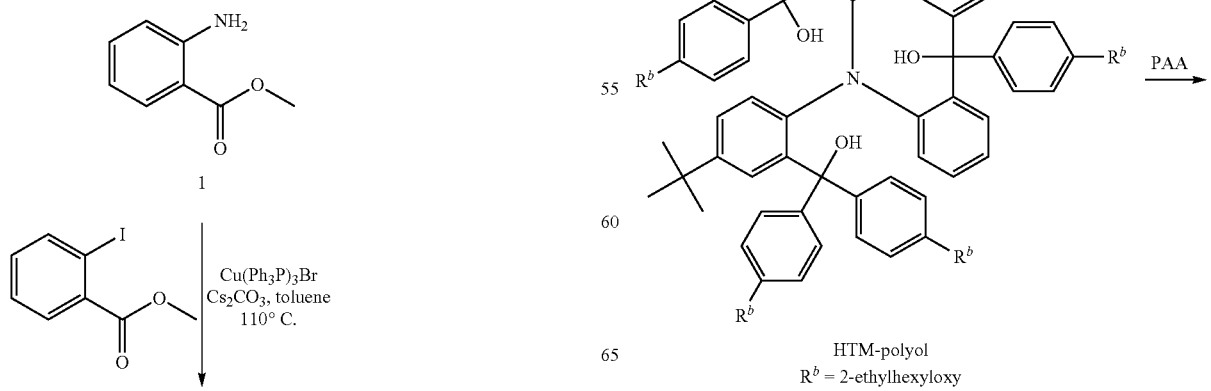

-continued

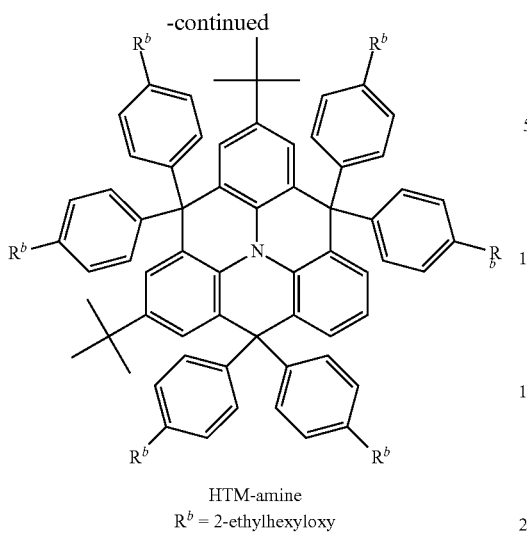

HTM-amine
$R^b$ = 2-ethylhexyloxy

Step 1: Preparation of dimethyl 2,2'-azanediyldibenzoate (2)

A mixture of methyl anthranilate (1) (2.00 g, 13.23 mmol), methyl 2-iodobenzoate (3.46 g, 13.23 mmol), Cu(Ph$_3$P)$_3$Br (2.46 g, 2.64 mmol), Cs$_2$CO$_3$ (6.46 g, 19.84 mmol), and toluene (90 ml) was reacted up to 110° C. under nitrogen atmosphere for 24 hours. After the reaction was completed, a reaction mixture was cooled to room temperature and solvent was removed by distillation under reduced pressure. Remaining reaction material was extracted with ethyl acetate (EA) and water, and an organic material layer was washed with brine. Then, moisture was removed with anhydrous Na$_2$SO$_4$, and solvent was removed by distillation under reduced pressure, and the product was separated by column chromatography using EA/hexane (9:1) as an eluent to obtain dimethyl 2,2'-azanediyldibenzoate (2) as a white product (1.90 g, 51%). $^1$H NMR (300 MHz, CDCl$_3$, δ): 11.06 (s, 1H), 7.98 (d, J=8.4 Hz, 2H), 7.54 (d, J=8.4 Hz, 2H), 7.36 (t, J=7.2 Hz, 2H), 6.89 (t, J=7.5 Hz, 2H), 3.94 (s, 6H).

Step 2: Preparation of dimethyl 6,6'-azanediylbis(3-tert-butylbenzoate) (3)

Dimethyl 2,2'-azanediyldibenzoate (2) (1.00 g, 3.50 mmol) was dissolved in tert-butyl chloride (30 mL) and anhydrous AlCl$_3$ (65.5 mg, 0.49 mmol) was slowly added thereto. The reaction mixture was refluxed for 6 hours, and after the reaction was completed, solvent was removed by distillation under reduced pressure. The product was separated by column chromatography using EA/hexane (9:1) as an eluent to obtain dimethyl 6,6'-azanediylbis(3-tert-butylbenzoate) (3) as a yellow product (1.00 g, 72%). $^1$H NMR (300 MHz, CDCl$_3$, δ): 10.87 (s, 1H), 7.96 (d, J=2.1 Hz, 2H), 7.49-7.46 (m, 2H), 7.41-7.37 (m, 2H), 3.94 (s, 6H), 1.32 (s, 18H).

Step 3: Preparation of dimethyl 6,6'-(2-(methoxycarbonyl)phenylazanediyl)bis (3-tert-butylbenzoate) (4)

Dimethyl 6,6'-azanediylbis(3-tert-butylbenzoate) (3) (1.00 g, 2.51 mmol), methyl 2-iodobenzoate (0.65 mL, 4.27 mmol), K$_2$CO$_3$ (0.71 g, 5.14 mmol), Cu (28 mg, 0.441 mmol) and CuI (191 mg, 1.0 mmol) were dissolved in diphenylether (20 mL), and reacted at 190° C. under nitrogen atmosphere for 48 hours. When the reaction was completed, the reaction mixture was cooled to room temperature and the product was separated by column chromatography using EA/hexane (1.5:8.5) as an eluent to obtain dimethyl 6,6'-(2-(methoxycarbonyl)phenylazanediyl)bis(3-tert-butylbenzoate) (4) as a yellow product (1.00 g, 75%). $^1$H NMR (300 MHz, CDCl$_3$, δ): 7.57 (dd, J=2.4, 7.5 Hz, 2H), 7.52 (dd, J=1.8, 8.1 Hz, 1H), 7.39-7.36 (m, 2H), 7.34-7.28 (m, 1H), 7.02-6.99 (m, 4H), 3.37 (s, 3H), 3.35 (s, 3H), 3.31 (s, 3H), 1.29 (s, 18H).

Step 4: Preparation of HTM-Polyol 1-bromo-4-(2-ethylhexyloxy)benzene (2.15 g, 7.53 mmol) was dissolved in THF (20 mL), and n-BuLi (2.5 M in hexanes, 4.7 mL, 11.76 mmol) was slowly added dropwise at −78° C. The reaction mixture was stirred for 1 hour, and dimethyl 6,6'-(2-(methoxycarbonyl)phenylazanediyl) bis(3-tert-butylbenzoate) (4) (500 mg, 0.941) was dissolved in THF (5 mL), and slowly added dropwise at −78° C. The reaction mixture was stirred for 12 hours while slowly raising a temperature to room temperature, and when the reaction was completed, a cold water/saturated NH$_4$Cl solvent was added to complete the reaction. Then, an organic material layer was separated by EA, and washed with water and brine. Moisture of the organic material layer was removed with anhydrous Na$_2$SO$_4$, and the product was separated by column chromatography using EA/hexane (0.5: 9.5) as an eluent to obtain HTM-polyol as a yellow compound.

$^1$H NMR (300 MHz, CDCl$_3$, δ): 7.57-7.54 (m, 4H), 7.46-7.40 (m, 8H), 7.13-6.90 (m, 8H), 6.79-6.56 (m, 14H), 3.79 (d, J=5.4 Hz, 6H), 3.71 (d, J=5.4 Hz, 6H), 1.70 (m, 6H), 1.30 (s, 18H), 1.53-1.31 (m, 48H), 0.93-0.87 (m, 36H).

Step 5: Preparation of HTM-Amine

Polyphosphoric acid (PPA) (2 mL) was added to HTM-polyol (100 mg, 0.06 mmol), followed by stirring at 35° C. for 6 hours. After the reaction was completed, the reaction mixture was neutralized with distilled water. Then, the produced solid compound was filtered, washed with water, dissolved in methylene chloride, and neutralized with NaHCO$_3$ and washed with water and brine. Finally, moisture of the organic material layer was removed with anhydrous Na$_2$SO$_4$, and solvent was removed by distillation under reduced pressure, and the product was separated by column chromatography using EA/hexane (0.2:9.8) as an eluent to obtain HTM-amine as a yellow product.

$^1$H NMR (300 MHz, CDCl$_3$, δ): 7.12-7.06 (m, 19H), 6.96-6.80 (m, 12H), 3.79 (d, J=5.4 Hz, 6H), 3.71 (d, J=5.4 Hz, 6H), 1.76 (m, 6H), 1.32 (s, 18H), 1.53-1.31 (m, 48H), 0.93-0.87 (m, 36H).

[Example 2] Preparation of Si-HTM-Polyol and Si-HTM-Amine that are Hole Transporting Materials

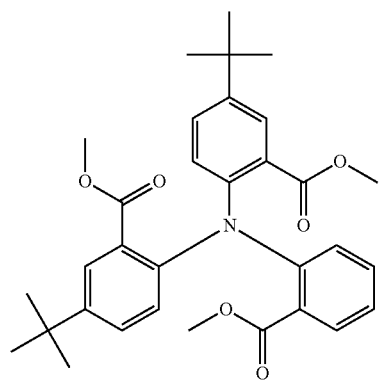

4

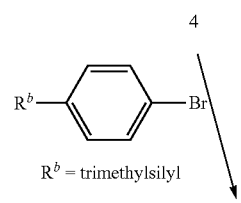

$R^b$ = trimethylsilyl

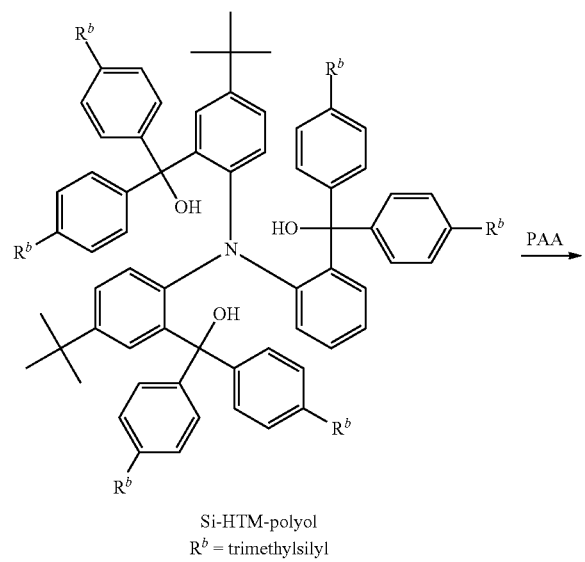

Si-HTM-polyol
$R^b$ = trimethylsilyl

PAA →

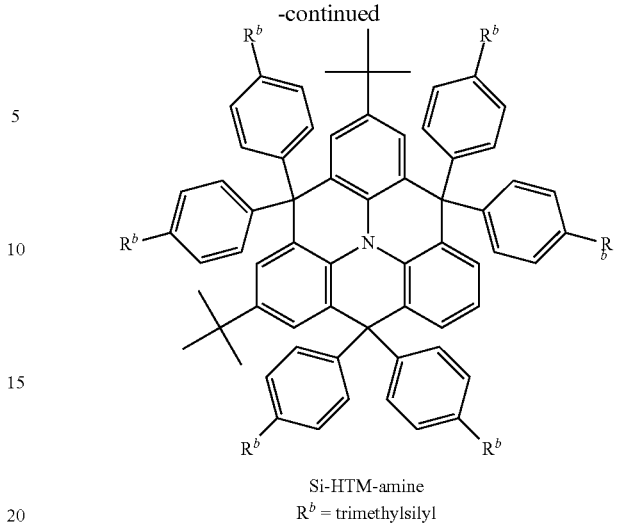

Si-HTM-amine
$R^b$ = trimethylsilyl

Preparation of Si-HTM-Polyol

Si-HTM-polyol was obtained by the same reaction method as step 4 of Example 1 above except for using 1-bromo-4-trimethylsilylbenzene (1.74 g, 7.53 mmol) instead of using 1-bromo-4-(2-ethylhexyloxy)benzene of step 4 of Example 1 above.

$^1$H NMR (300 MHz, CDCl$_3$, δ): 7.57-7.46 (m, 5H), 7.41-7.39 (m, 8H), 7.24-7.0 (m, 12H), 6.95-6.90 (m, 3H), 6.83 (d, J=9 Hz, 6H), 1.27 (s, 18H), 0.25 (s, 54H).

Preparation of Si-HTM-Amine

Si-HTM-amine was obtained by the same reaction method as step 5 of Example 1 above except for using Si-HTM-polyol (100 mg, 0.06 mmol) instead of using the HTM-polyol of step 5 of Example 1 above.

$^1$H NMR (300 MHz, CDCl$_3$, δ): 7.51-7.42 (m, 4H), 7.41-7.39 (m, 8H), 7.21-6.93 (m, 13H), 6.83 (d, J=9 Hz, 6H), 1.28 (s, 18H), 0.26 (s, 54H).

Examples 3 to 6: Manufacture of Perovskite Solar Cell

[Example 3] Manufacture of Perovskite Solar Cell Including HTM-Polyol Hole Transport Layer 1-1

A perovskite solar cell including the compound HTM-polyol of Example 1 as the hole transport layer was manufactured, and specifically, the perovskite solar cell was manufactured by the following steps.

Step 1: An ITO substrate was subjected to spin-coating at 3000 rpm for 30 seconds with a zinc oxide (ZnO) aqueous solution to form a zinc oxide layer having a thickness of 50 nm, followed by thermal treatment at 150° C. for 10 minutes.

Step 2: A zinc oxide layer was subjected to spin-coating at 6000 rpm for about 30 seconds with a PbI$_2$ (lead iodide) 0.87M (400 mg/mL in DMF) solution, and dried in 100° C. hot plate for 5 minutes.

Step 3: A layer coated with lead iodide was subjected to spin-coating at 6000 rpm for 30 seconds with a solution in which 40 mg of CH$_3$NH$_3$I (methyl ammonium iodide) was dissolved in 1 mL of isopropylalcohol (IPA), and dried in 100° C. hot plate for 1 minute.

Step 4: The MAPbI$_3$/ZnO/ITO film of step 3 was subjected to spin-coating at 4000 rpm for 30 seconds with the hole transporting material (HTM-polyol)/chlorobenzene solution (72.3 mg/mL) prepared in Example 1 so that the hole transport layer was formed in a thickness of 200 nm.

Step 5: A silver (Ag) electrode having a thickness of 120 nm was formed on the HTM/MAPbI$_3$/ZnO/ITO film of step 4 above through a thermal evaporator.

[Example 4] Manufacture of Perovskite Solar Cell Including HTM-Polyol Hole Transport Layer 1-2

A perovskite solar cell including the compound HTM-polyol of Example 1 as the hole transport layer was manufactured by the same method as Example 3, except that Li-TFSI (17.5 μL) and t-BP (28.5 μL) were additionally added as additives in step 4 of Example 3.

[Example 5] Manufacture of Perovskite Solar Cell Including HTM-Amine Hole Transport Layer 2-1

A perovskite solar cell including the compound HTM-amine of Example 1 as the hole transport layer was manufactured by the same method as Example 3, except that HTM-amine was used as the hole transporting material instead of using the HTM-polyol.

[Example 6] Manufacture of Perovskite Solar Cell Including HTM-Amine Hole Transport Layer 2-2

A perovskite solar cell including the compound HTM-amine of Example 1 as the hole transport layer was manufactured by the same method as Example 4, except that HTM-amine was used as the hole transporting material instead of using the HTM-polyol.

Examples 7 to 8 and Comparative Example 1: Manufacture of Perovskite Solar Cell

[Example 7] Manufacture of Organic Solar Cell Including HTM-Polyol Hole Transport Layer 1

An organic solar cell including the compound HTM-polyol of Example 1 as the hole transport layer was manufactured, and specifically, the organic solar cell was manufactured by the following steps.

Step 1: An ITO substrate was subjected to spin-coating at 3000 rpm for 30 seconds with a zinc oxide (ZnO) aqueous solution to form a zinc oxide layer having a thickness of 50 nm, followed by thermal treatment at 150° C. for 10 minutes.

Step 2: Phenyl-C71-butyric acid methyl ester (12 mg) and poly[4,8-bis[(2-ethylhexyl) oxy]benzo[1,2-b:4,5-b']dithiophene-2,6-diyl][3-fluoro-2-[(2-ethylhexyl)carbonyl]thieno[3,4-b]thiophenediyl] (PTB7) (8 mg) were mixed in chlorobenzene (CB) (0.97 mL), respectively, and 1,8-diiodooctane (DIO) solution (0.03 mL) was added thereto, followed by stirring at 60° C. for 12 hours, and a photoactive layer having a thickness of 100 nm was manufactured on the ZnO conductive film.

Step 3: The hole transporting material (HTM-polyol) (0.5 mg) prepared in Example 1 was diluted in IPA (10 mL), and then, a P-type conductive film having a very thin thickness was manufactured on the photoactive layer.

Step 4: A silver (Ag) electrode having a thickness of 120 nm was formed on the HTM/photoactive layer/ZnO/ITO film of step 3 above through a thermal evaporator.

[Example 8] Manufacture of Organic Solar Cell Including HTM-Amine Hole Transport Layer 2

An organic solar cell including the compound HTM-amine of Example 1 as the hole transport layer was manufactured by the same method as Example 7, except that HTM-amine was used as the hole transporting material instead of using the HTM-polyol.

[Comparative Example 1] Manufacture of Organic Solar Cell Including HTM-Amine Hole Transport Layer An organic solar cell including PEDOT:PSS (poly(3,4-ethylenedioxythiophene):poly(styrenesulfonate)) as the hole transport layer was manufactured by the same method as Example 7, except that PEDOT:PSS was used as the hole transporting material instead of using the HTM-polyol.

[Experimental Example 1] UV-Visible Light Absorption and Fluorescence Spectra

Figure 3:
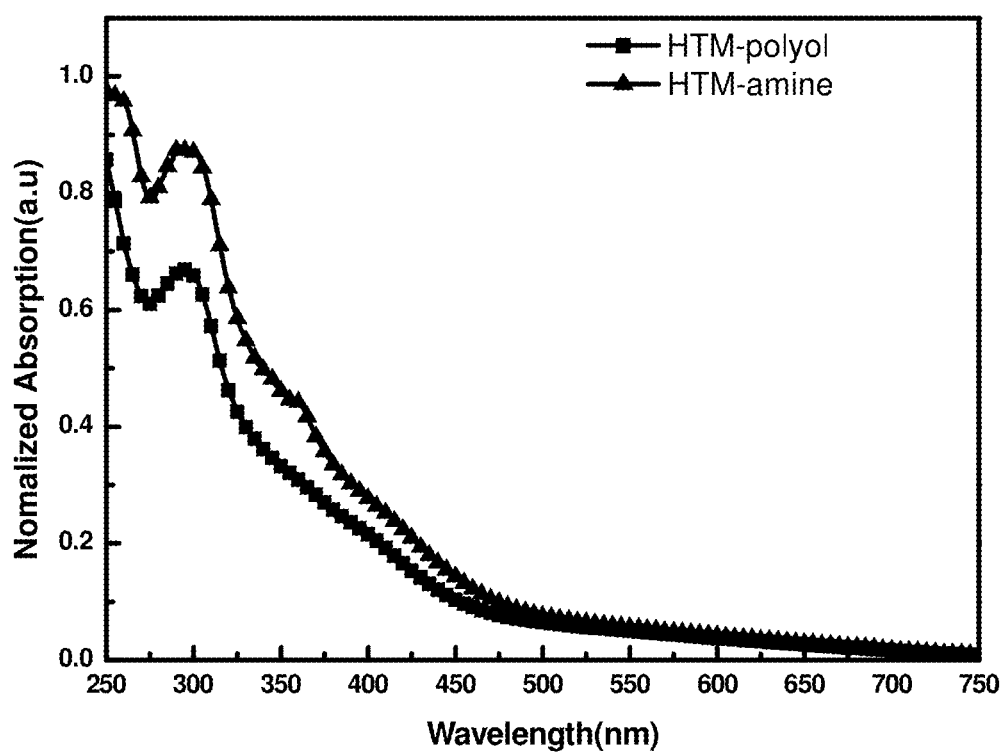
FIG. 3 is a graph illustrating UV-visible absorption spectra of HTM-polyol and HTM-amine prepared by Example 1.
Figure 4:
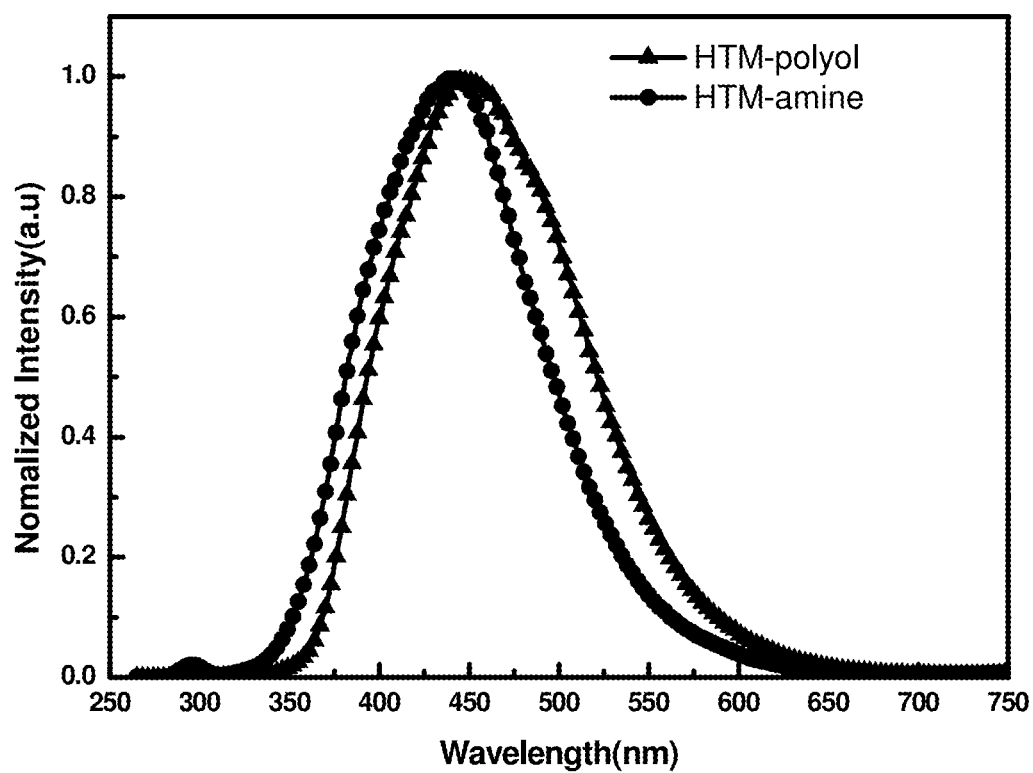
FIG. 4 is a graph illustrating fluorescence spectra of the HTM-polyol and the HTM-amine prepared by Example 1 in a chloroform solution state.

UV-visible light absorption and fluorescence spectra of the HTM-polyol and the HTM-amine that are the hole transporting materials prepared by Example 1 were measured in chloroform aqueous solution (1×10$^{-5}$M) by absorption spectrophotometer (JASCO, V-570), and results thereof were illustrated in FIGS. 3 and 4.

As illustrated in FIG. 3, the absorption maximum ($\lambda_{max}^a$) at the absorption-emission spectra of the HTM-polyol and the HTM-amine in the chloroform aqueous solution was measured to be about 300 nm. In addition, as illustrated in FIG. 4, the emission maximum ($\lambda_{max}^b$) at the fluorescence spectra of the HTM-polyol and the HTM-amine in the chloroform aqueous solution was measured to be 440 nm.

[Experimental Example 2] Cyclic Voltammetry

In order to find out the HOMO and the LUMO energy level of the HTM-polyol and the HTM-amine that are the hole transporting materials prepared in Example 1, the energy levels thereof were measured by using a cyclic voltammetry. Results thereof were illustrated in FIGS. 5 and 6.

Figure 5:
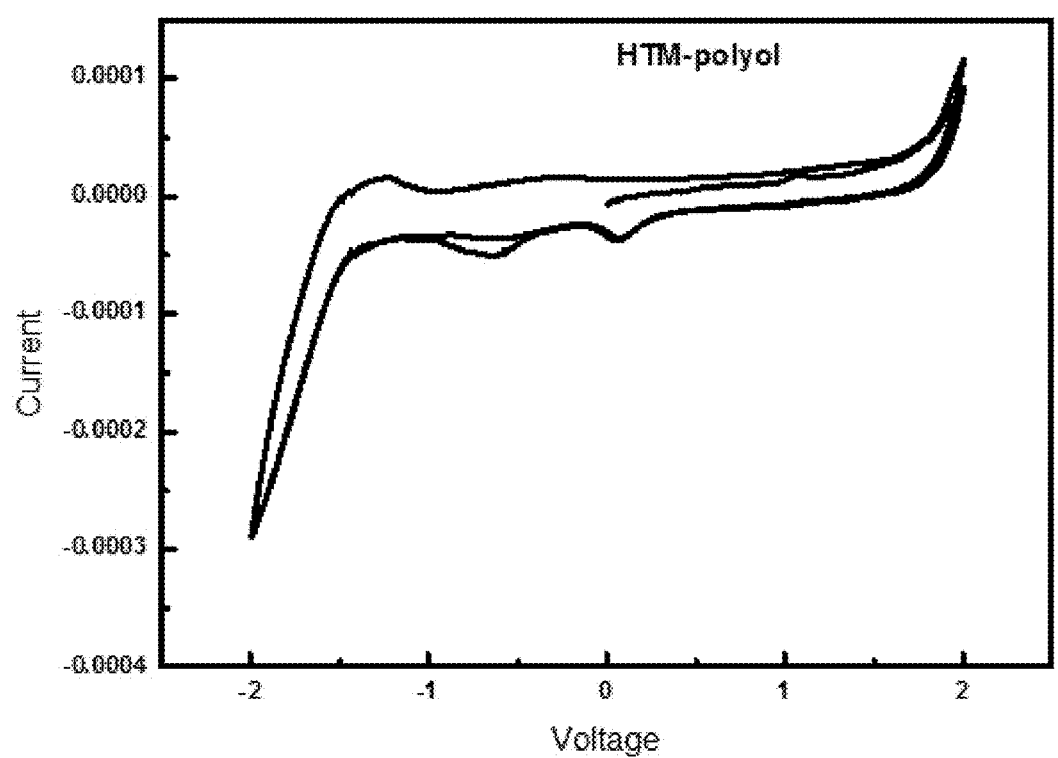
FIG. 5 is a graph illustrating cyclic voltammetry of the HTM-polyol prepared by Example 1.
Figure 6:
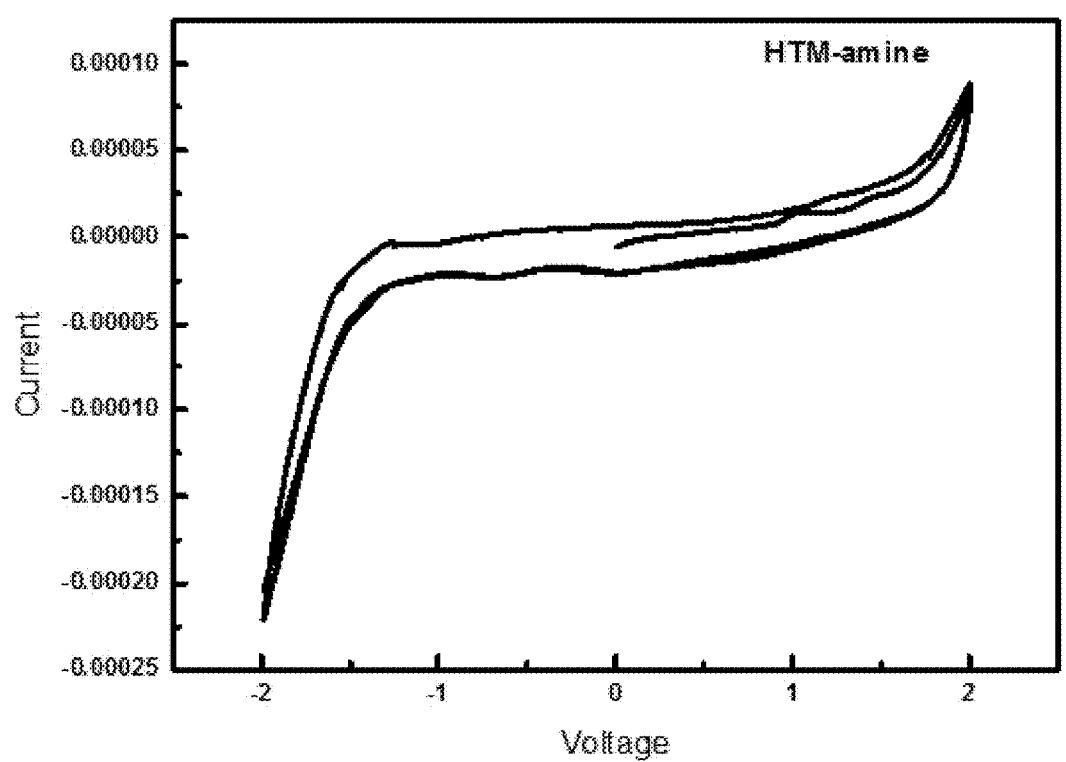
FIG. 6 is a graph illustrating cyclic voltammetry of the HTM-amine prepared by Example 1.

As illustrated in FIGS. 5 and 6, reversible oxidation and reduction reaction was exhibited in both of the two compounds, and in particular, the HTM-polyol had an oxidization peak at 0.97 V, and the HTM-amine had an oxidization peak at 0.90 V.

Figure 2:
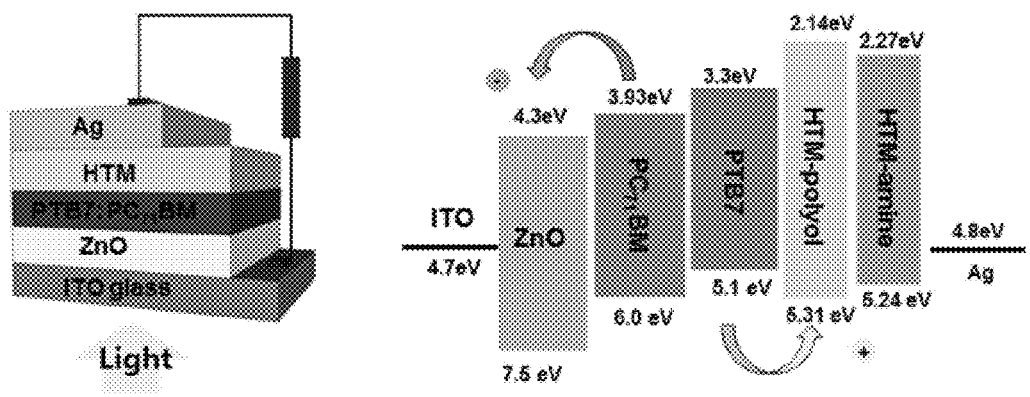
FIG. 2 is a chart illustrating a structure and an energy level of an inverted organic solar cell.

Meanwhile, HOMO and LUMO energy level diagrams of the HTM-polyol and the HTM-amine that are the hole transporting materials prepared in Example 1 were illustrated in FIGS. 1 and 2. The HOMO and the LUMO of the HTM-polyol were measured to be −5.31 and −2.14 eV, respectively, and the HOMO and the LUMO of the HTM-amine were measured to be −5.24 and −2.27 eV, respectively. From the above results, optical band gaps ($Eg^{opt\ c}$) of the HTM-polyol and the HTM-amine that are the hole transporting materials prepared in Example 1 were calculated to be 3.17 eV and 2.97 eV, respectively.

That is, the HOMO energy level of the HTM-polyol and the HTM-amine that are the hole transporting materials prepared in Example 1 thoroughly fitted with the energy level of CH$_3$NH$_3$PbI$_3$ (−5.43 eV) that could be included in the perovskite layer of the solar cell, such that favorable charge separation and charge transfer at the interface of the perovskite layer and the hole transport layer could be expected.

Accordingly, it could be appreciated that as compared to the spiro-OMeTAD (HOMO, −5.22 eV) which is the currently and generally used hole transporting material, the HOMO energy level of the present invention is more easily and effectively moved from the perovskite layer to the HTM-polyol (Example 1) or the HTM-amine (Example 1) which is the material of the hole transport layer. Therefore, it could be expected from harmony of the HOMO level that the triphenylamine derivative of the present invention has much high power conversion efficiency as compared to the existing spiro-OMeTAD.

[Experimental Example 3] Measurement of Thermogravimetric Analysis

In order to research thermal properties of the HTM-polyol and the HTM-amine that are the hole transporting materials prepared in Example 1, decomposition temperatures of the HTM-polyol and the HTM-amine were measured by a thermal gravimetric analyzer (TGA, Mettler Toledo, TGA/SDTA). Results thereof were illustrated in FIGS. 7 and 8.

Figure 7:
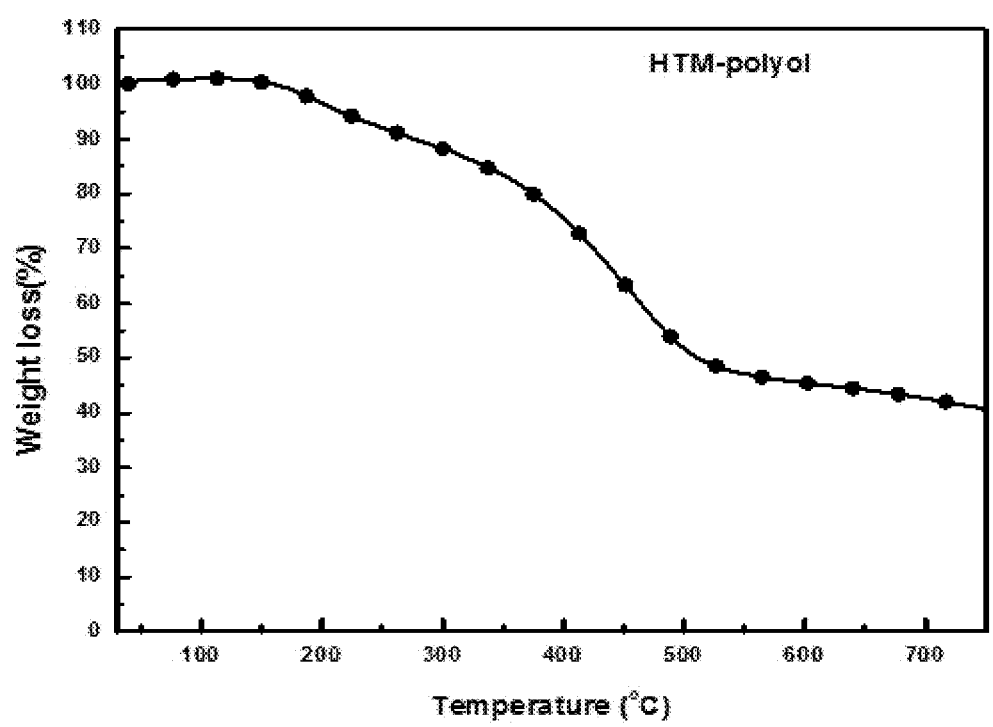
FIG. 7 is a thermogravimetric analysis graph of the HTM-polyol prepared by Example 1.
Figure 8:
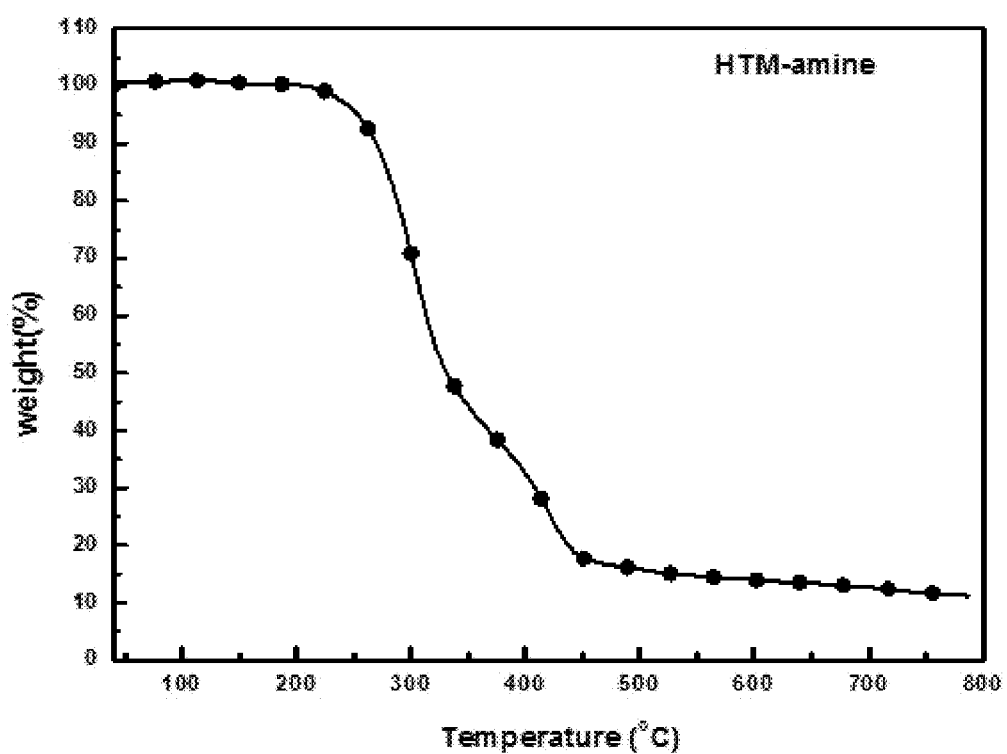
FIG. 8 is a thermogravimetric analysis graph of the HTM-amine prepared by Example 1.
Figure 9:
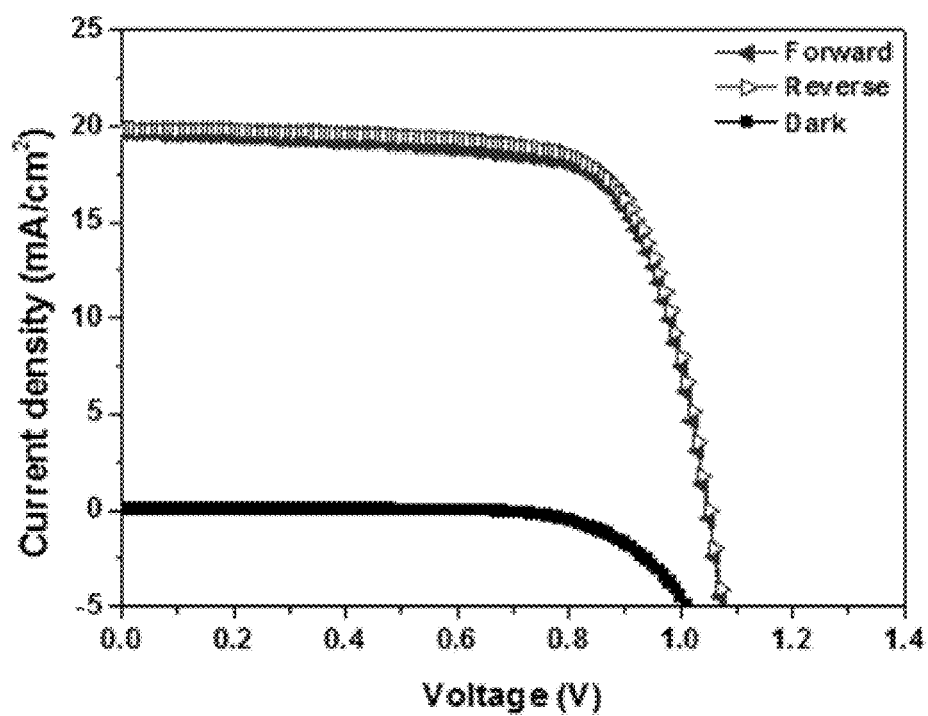
FIG. 9 is a graph illustrating a photocurrent density-voltage (J-V) curve of the perovskite solar cell (Example 3) without a dopant of the HTM-polyol which is a hole transporting material.
Figure 10:
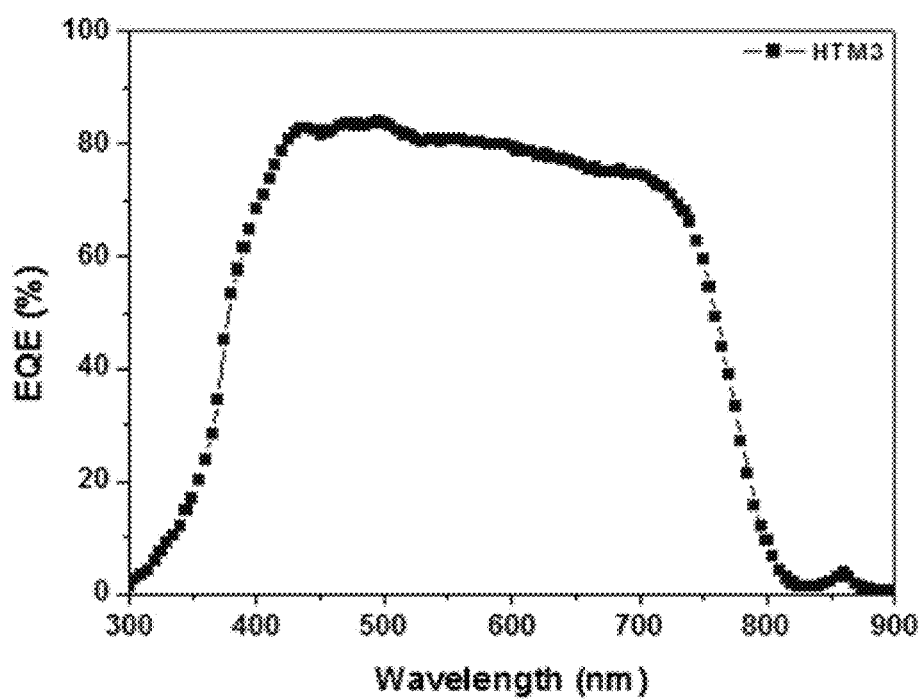
FIG. 10 is a graph illustrating an external quantum efficiency curve of the perovskite solar cell (Example 3) without the dopant of the HTM-polyol which is the hole transporting material.
Figure 11:
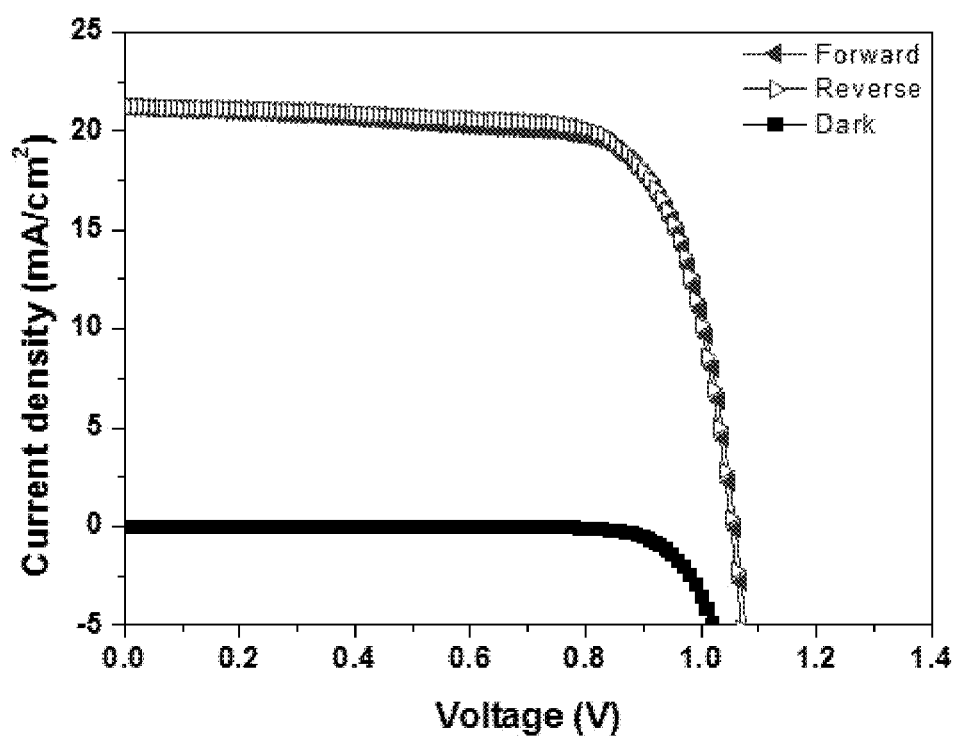
FIG. 11 is a graph illustrating a photocurrent density-voltage (J-V) curve of the perovskite solar cell (Example 4) to which the dopant of the HTM-polyol which is a hole transporting material is added.
Figure 12:
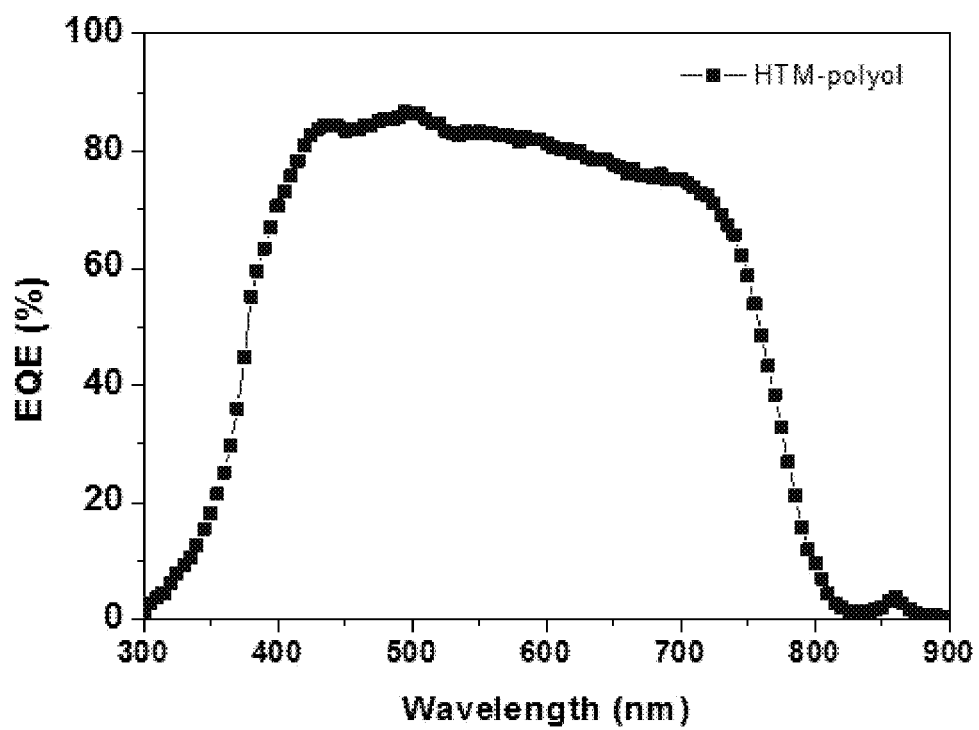
FIG. 12 is a graph illustrating an external quantum efficiency curve of the perovskite solar cell (Example 4) to which the dopant of the HTM-polyol which is the hole transporting material is added.
Figure 13:
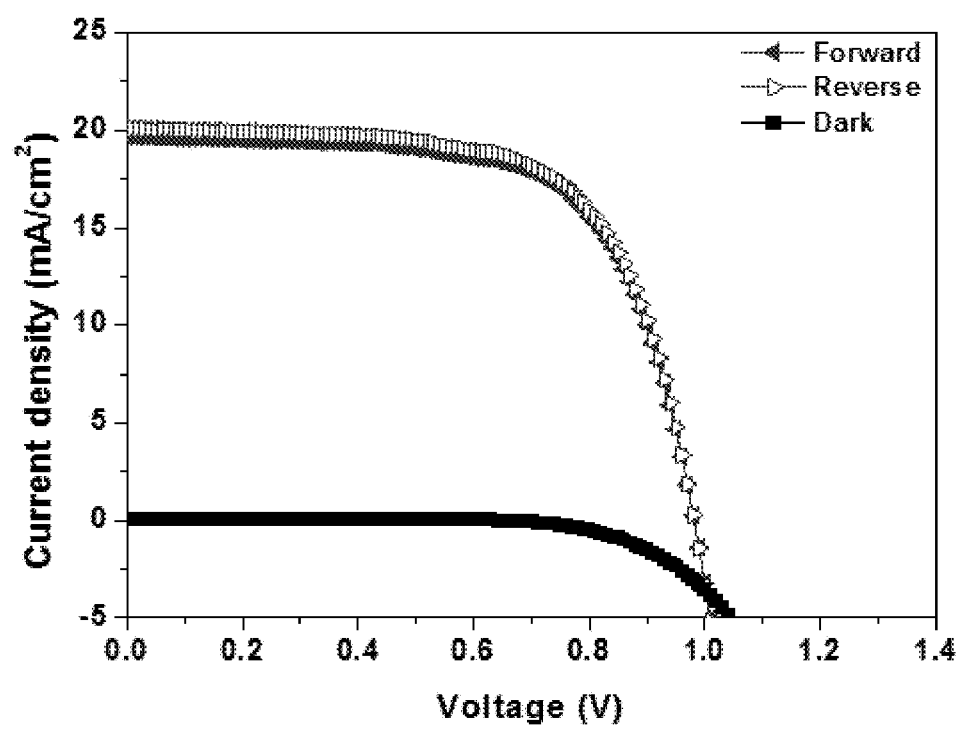
FIG. 13 is a graph illustrating a photocurrent density-voltage (J-V) curve of the perovskite solar cell (Example 5) without a dopant of the HTM-amine which is a hole transporting material.
Figure 14:
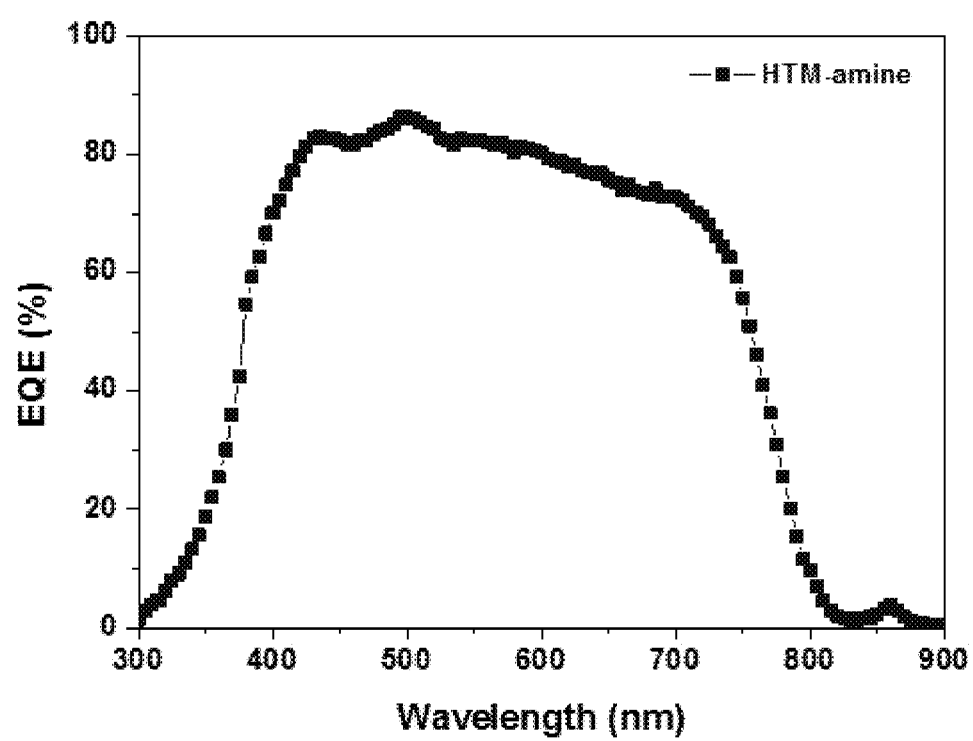
FIG. 14 is a graph illustrating an external quantum efficiency curve of the perovskite solar cell (Example 5) without the dopant of the HTM-amine which is the hole transporting material.
Figure 15:
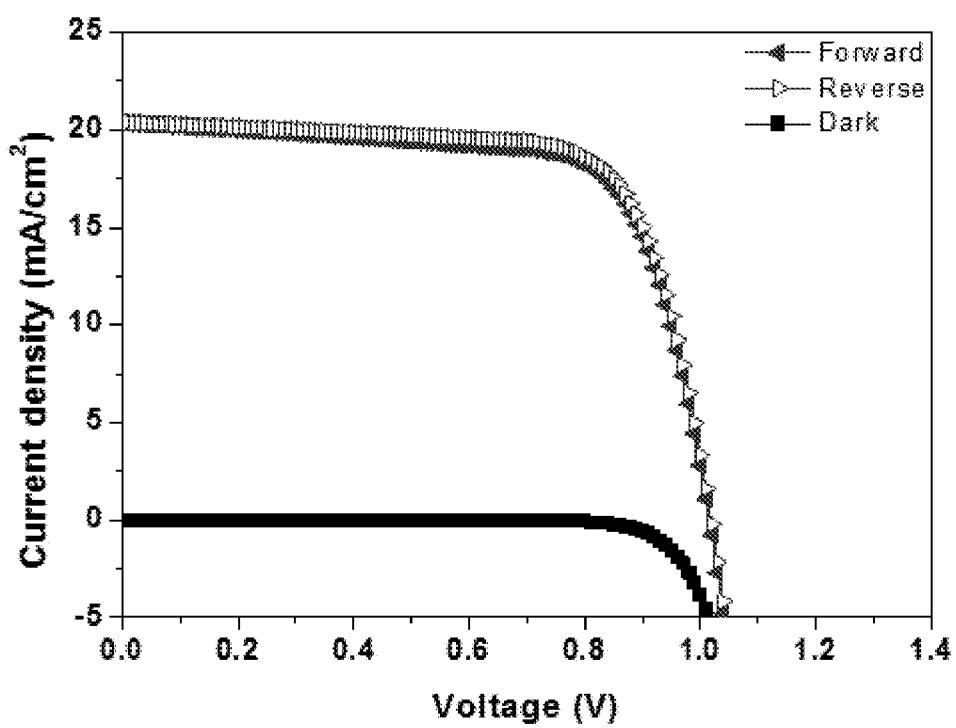
FIG. 15 is a graph illustrating a photocurrent density-voltage (J-V) curve of the perovskite solar cell (Example 6) to which the dopant of the HTM-amine which is the hole transporting material is added.
Figure 16:
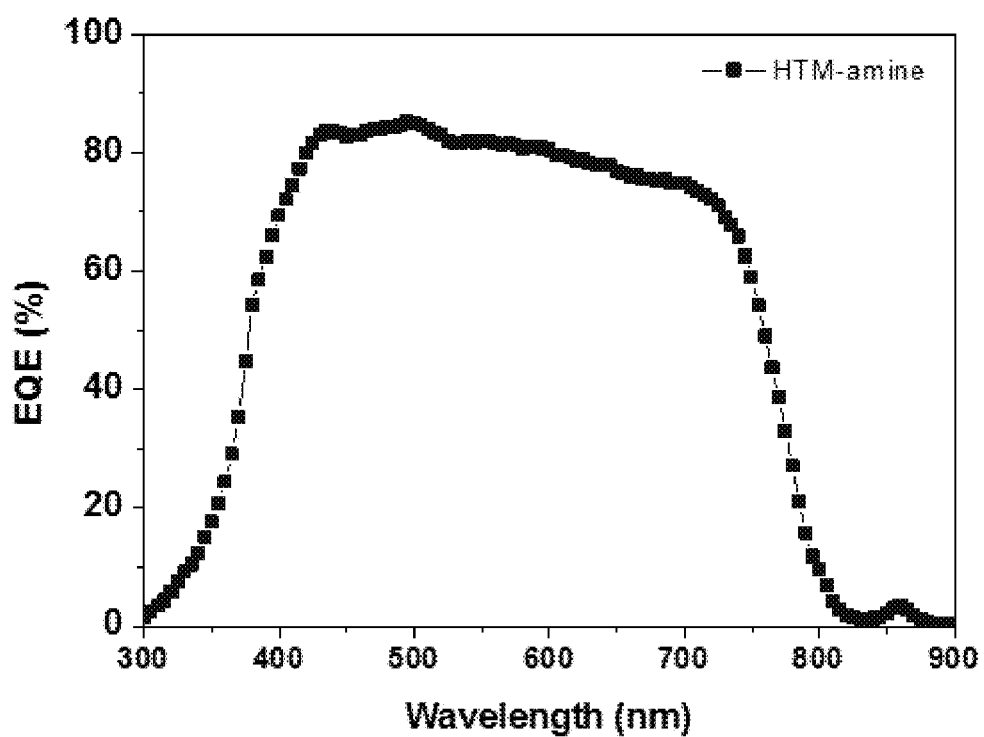
FIG. 16 is a graph illustrating an external quantum efficiency curve of the perovskite solar cell (Example 6) to which the dopant of the HTM-amine which is the hole transporting material is added.

It could be appreciated from FIGS. 7 and 8 that the decomposition temperatures (Td) at which 5% of decomposition in a weight ratio of the HTM-polyol and the HTM-amine started were high as 215° C. and 254° C., respectively. That is, these high decomposition temperatures indicated that two compounds are thermally stable.

It could be appreciated from the analysis results that the triphenylamine derivative which is the hole transporting material of the present invention is capable of forming a stable film, particularly, a thermally stable amorphous film.

[Experimental Example 4] Characteristics of Perovskite Solar Cell Depending on Kinds of Hole Transporting Material Photocurrent density-voltage (J-V) and current conversion efficiency (IPCE) curves of the perovskite solar cells of Examples 3, 4, 5, and 6 were analyzed by a solar simulator, and results thereof were illustrated in FIGS. 9 to 16. In addition, a power conversion efficiency (PCE) of the perovskite solar cells of Examples 3, 4, 5, and 6 was calculated from the open-circuit voltage (Voc), the short-circuit current (Jsc), and the fill factor (FF), and results thereof were illustrated in Table 1 below.

As illustrated in FIGS. 9 to 16, as analysis results of the current conversion efficiency (IPCE) of the perovskite solar cells of Examples 3, 4, 5, and 6, the current conversion efficiency (IPCE) of Example 3 was measured to be approximately 85%.

As illustrated in Table 1 below, the power conversion efficiency (PCE) of the perovskite solar cells of Examples 3, 4, 5, and 6 was analyzed, wherein an average value was deduced from the values obtained by repeating the measurements eight times under the same condition. Here, the power conversion efficiency of the solar cells of Examples 3, 4, 5, and 6 was measured to be 15.1% when the dopant was not added, and 16.5% when the dopant was added.

TABLE 1

| | Hole Transport Layer | | | $V_{oc}$ | $J_{sc}$ | FF | PCE |
|---|---|---|---|---|---|---|---|
| | HTM | Dopant | | [V] | [mA/cm$^2$] | [%] | (%) |
| Example 3 | HTM-polyol | — | forward | 1.04 | 19.7 | 71.7 | 14.7 |
| | | | reverse | 1.04 | 19.8 | 73.1 | 15.1 |
| Example 4 | HTM-polyol | Added | forward | 1.05 | 21.2 | 73.1 | 16.3 |
| | | | reverse | 1.05 | 21.2 | 74 | 16.5 |

TABLE 1-continued

| | Hole Transport Layer | | | $V_{oc}$ | $J_{sc}$ | FF | PCE |
|---|---|---|---|---|---|---|---|
| | HTM | Dopant | | [V] | [mA/cm$^2$] | [%] | (%) |
| Example 5 | HTM-amine | — | forward | 0.98 | 19.7 | 66.2 | 12.8 |
| | | | reverse | 0.98 | 20.1 | 67.1 | 13.2 |
| Example 6 | HTM-amine | Added | forward | 1.01 | 20.3 | 71.2 | 14.6 |
| | | | reverse | 1.01 | 20.4 | 73 | 15 |

Figure 17:
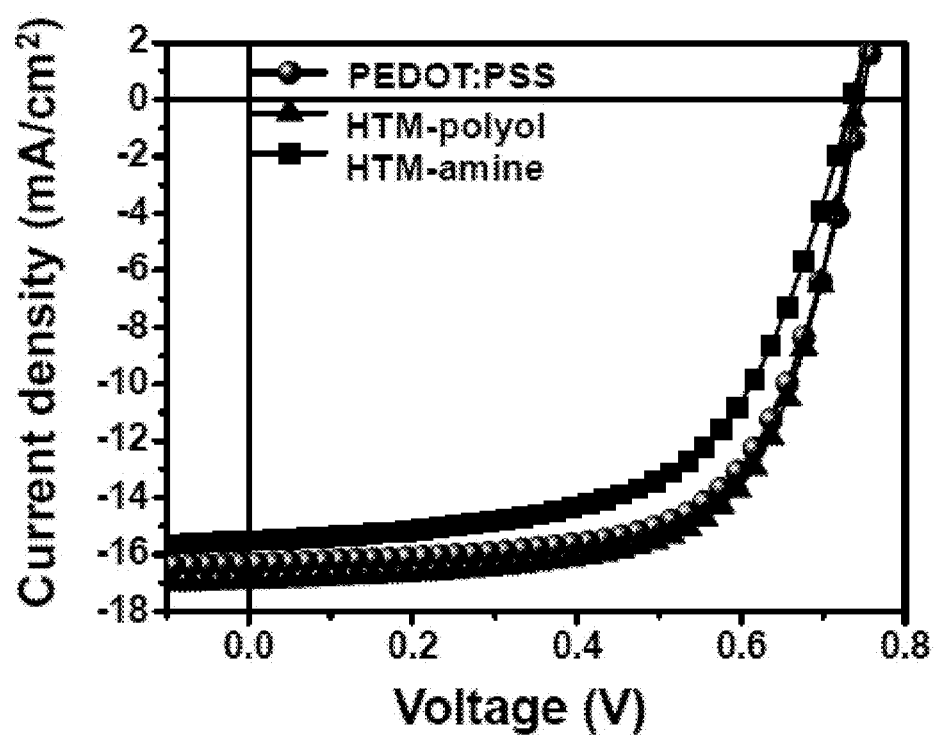
FIG. 17 is a graph illustrating photocurrent density-voltage (J-V) curves of inverted bulk heterojunction organic solar cells (Examples 7 and 8, and Comparative Example 1) according to the hole transporting material.
Figure 18:
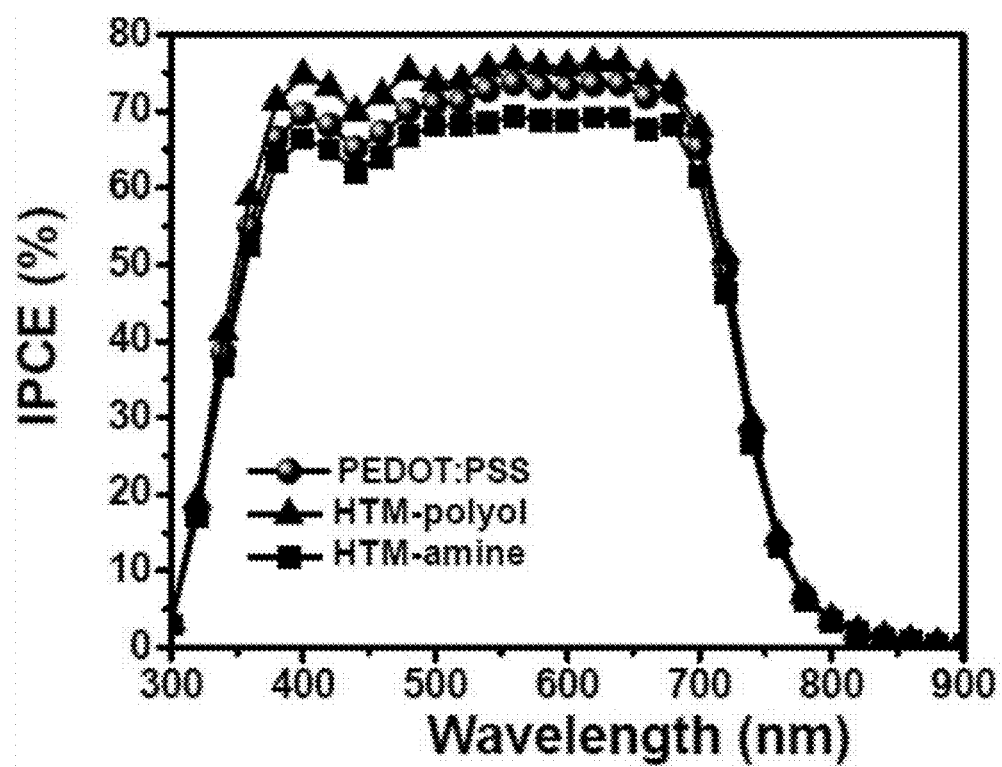
FIG. 18 is a graph illustrating external quantum efficiency curves of the inverted bulk heterojunction organic solar cells (Examples 7 and 8, and Comparative Example 1) according to the hole transporting material.

[Experimental Example 6] Characteristics of Bulk Heterojunction Organic Solar Cell Depending on Kinds of Hole Transporting Material Photocurrent density-voltage (J-V) and current conversion efficiency (IPCE) curves of the bulk heterojunction organic solar cells of Examples 7 and 8, and Comparative Example 1 were analyzed by a solar simulator, and analysis results thereof were illustrated in FIGS. 17 to 18. In addition, a power conversion efficiency (PCE) of the bulk heterojunction organic solar cells of Examples 7 and 8, and Comparative Example 1 was calculated from the open-circuit voltage (Voc), the short-circuit current (Jsc), and the fill factor (FF), and results thereof were illustrated in Table 2 below.

As illustrated in FIGS. 17 and 18, as analysis results of the photocurrent density-voltage (J-V) and current conversion efficiency (IPCE) of the bulk heterojunction organic solar cells of Examples 7 and 8, and Comparative Example 1, the PEDOT:PSS (Comparative Example 1) had a power conversion efficiency of 7.90%, but the HTM-polyol (Example 7) had an improved power conversion efficiency of 8.34%, and the current conversion efficiency (IPCE) was measured to be approximately 80%. It could be appreciated that the HTM-polyol had more improved values as compared to the PEDOT:PSS.

TABLE 2

| | HTM | $V_{oc}$ [V] | $J_{sc}$ [mA/cm$^2$] | FF [%] | PCE [%] |
|---|---|---|---|---|---|
| Example 7 | HTM-polyol | 16.70 ± 0.16 | 0.74 ± 0.02 | 65.95 ± 0.86 | 8.23 ± 0.11 |
| Comparative Example 1 | PEDOT:PSS | 16.29 ± 0.16 | 0.75 ± 0.01 | 64.37 ± 0.60 | 7.86 ± 0.04 |

The novel triphenylamine derivative according to the present invention is used as the material of the hole transport layer of the photovoltaic device, particularly, the perovskite solar cell and the organic solar cell to exhibit improved power conversion efficiency as compared to the existing hole transporting materials.

The triphenylamine derivative according to the present invention may have high hole mobility, an appropriate energy level, thermal stability, and excellent solubility to exhibit more excellent power conversion efficiency as compared to the existing hole transporting material of the perovskite solar cell, Spiro-OMeTAD.

Specifically, the triphenylamine derivative according to the present invention is a single molecule and is possible to be prepared and separated by a simple process, which is significantly favorable to commercial application, and has a high charge mobility as compared to the existing polymer hole transporting material. Therefore, when the triphenylamine derivative of the present invention is applied as the hole transporting material of solar cells, higher power conversion efficiency may be exhibited.

In addition, when an alcohol group is substituted in the triphenylamine derivative of the present invention, even though separate additives such as Li-TFSI, t-BP, etc., used to improve power conversion efficiency in the existing perovskite solar cell are not mixed to be used, excellent power conversion efficiency and lifespan characteristic may be exhibited.

Further, the triphenylamine derivative of the present invention is applied to an organic solar cell as the hole transporting material instead of using the existing PEDOT:PSS mixture showing a highly acidic characteristic, such that excellent power conversion efficiency and lifespan characteristic may be exhibited without causing corrosion of a lower electrode layer while not affecting other characteristics of the hole transport layer at all.

Therefore, the triphenylamine derivative of the present invention is effectively usable as the hole transporting material in photovoltaic device fields including the perovskite solar cell and the organic solar cell.

What is claimed is:

1. A triphenylamine derivative represented by Chemical Formula 2 or 3 below:

[Chemical Formula 2]

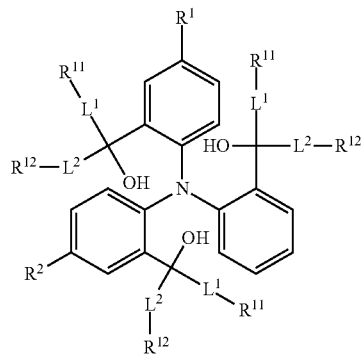

[Chemical Formula 3]

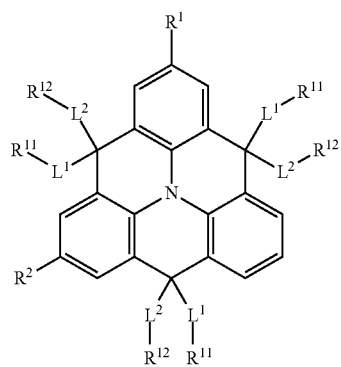

wherein $R^1$ and $R^2$ are each independently C1-20 alkyl; $L^1$ and $L^2$ are each independently C6-20 arylene; and $R^{11}$ and $R^{12}$ are each independently C1-20 alkoxy, or C1-20 alkylsilyl.

2. The triphenylamine derivative of claim 1, wherein $R^1$ and $R^2$ are each independently methyl, ethyl, propyl, butyl, pentyl or hexyl; $L^1$ and $L^2$ are each independently phenylene, biphenylene, terphenylene, naphthylene, phenanthrenylene, anthracenylene or perylenylene; and $R^{11}$ and $R^{12}$ are each independently methoxy, ethoxy, propoxy, butoxy, pentoxy, hexyloxy, ethylhexyloxy, trimethylsilyl, triethylsilyl or methylethylsilyl.

3. The triphenylamine derivative of claim 2, wherein the triphenylamine derivative is selected from the following structures:

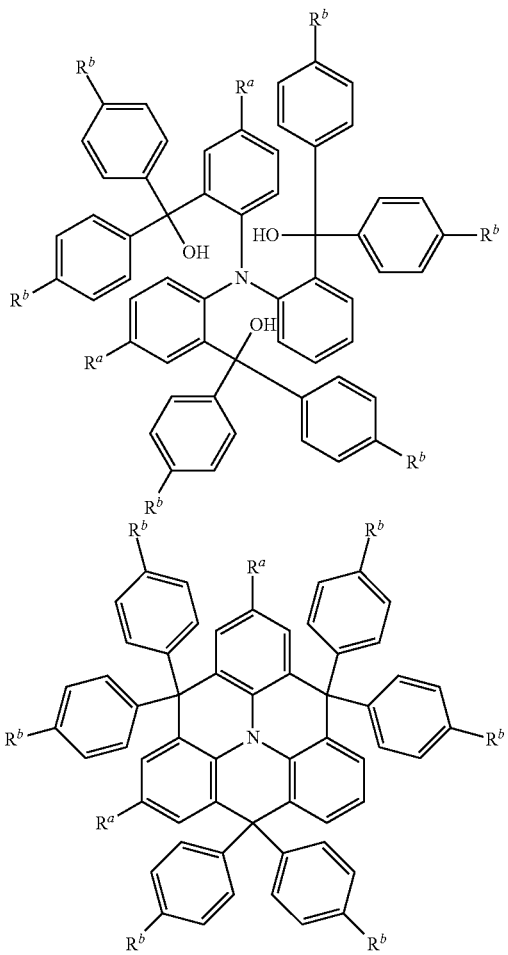

$R^a$ is butyl, and $R^b$ is ethylhexyloxy or trimethylsilyl.

4. A photovoltaic device comprising the triphenylamine derivative of claim 1.

5. The photovoltaic device of claim 4, wherein the triphenylamine derivative is a hole transporting material.

6. The photovoltaic device of claim 4, wherein the photovoltaic device is an organic/inorganic hybrid perovskite solar cell, an organic solar cell, an organic light-emitting diode, or a photodetector.

7. The photovoltaic device of claim 6, wherein the organic/inorganic hybrid perovskite solar cell further contains an additive selected from the group consisting of t-BP (t-butyl pyridine), Li-TFSI (lithium bis(trifluoro methanesulfonyl)imide), and combinations thereof.

* * * * *